(12) United States Patent
Rosenberg et al.

(10) Patent No.: US 8,545,858 B2
(45) Date of Patent: *Oct. 1, 2013

(54) POROUS CALCIUM PHOSPHATE BONE MATERIAL

(75) Inventors: Aron D. Rosenberg, Brookline, MA (US); Laurent D. Gillès de Pélichy, Fréjus (FR); Shrikar Bondre, Monmouth Junction, NJ (US); Michael Strunk, Woburn, MA (US)

(73) Assignee: Etex Corporation, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/438,207

(22) Filed: Apr. 3, 2012

(65) Prior Publication Data

US 2012/0282301 A1    Nov. 8, 2012

Related U.S. Application Data

(63) Continuation of application No. 11/294,819, filed on Dec. 6, 2005, now Pat. No. 8,147,860.

(51) Int. Cl.
*A61K 9/12* (2006.01)
*A61K 9/00* (2006.01)
*A61K 48/00* (2006.01)
*A61K 9/46* (2006.01)
*A61K 33/42* (2006.01)
*A61K 33/24* (2006.01)
*A61K 38/18* (2006.01)

(52) U.S. Cl.
USPC ........ 424/400; 424/466; 424/184.1; 424/649; 424/602; 424/423; 424/44

(58) Field of Classification Search
USPC ............... 424/400, 44, 423, 466, 184.1, 649, 424/602
See application file for complete search history.

(56) References Cited

U.S. PATENT DOCUMENTS

| | | | |
|---|---|---|---|
| 2,967,802 A | 1/1961 | Towey et al. | |
| 3,577,492 A * | 5/1971 | Welsh et al. | 264/120 |
| 3,608,071 A | 9/1971 | Relyveld et al. | |
| 3,925,545 A | 12/1975 | Relyveld | |
| 4,016,252 A | 4/1977 | Relyveld | |
| 4,093,576 A * | 6/1978 | deWijn | 523/114 |
| 4,108,690 A | 8/1978 | Heller | |
| 4,110,432 A | 8/1978 | Wilkinson et al. | |
| 4,157,378 A | 6/1979 | Tomlinson et al. | |
| 4,329,332 A | 5/1982 | Couvreur et al. | |
| 4,346,709 A | 8/1982 | Schmitt | |
| 4,347,234 A | 8/1982 | Wahlig et al. | |
| 4,353,888 A | 10/1982 | Sefton | |
| 4,429,691 A | 2/1984 | Niwa et al. | |
| 4,609,327 A | 9/1986 | Nishimori | |
| 4,612,053 A | 9/1986 | Brown et al. | |
| 4,620,327 A | 11/1986 | Caplan et al. | |
| 4,684,673 A | 8/1987 | Adachi | |
| 4,737,411 A | 4/1988 | Graves, Jr. et al. | |
| 4,842,603 A | 6/1989 | Draenert | |
| 4,849,193 A | 7/1989 | Palmer et al. | |
| 4,880,610 A | 11/1989 | Constantz | |
| 4,892,538 A | 1/1990 | Aebischer et al. | |
| RE33,161 E | 2/1990 | Brown et al. | |
| 4,917,702 A | 4/1990 | Scheicher et al. | |
| RE33,221 E | 5/1990 | Brown et al. | |
| 4,938,938 A | 7/1990 | Ewers et al. | |
| 4,959,104 A | 9/1990 | Iino et al. | |
| 5,007,930 A | 4/1991 | Dorman et al. | |
| 5,034,059 A | 7/1991 | Constantz | |
| 5,037,639 A | 8/1991 | Tung | |
| 5,041,138 A | 8/1991 | Vacanti et al. | |
| 5,047,031 A | 9/1991 | Constantz | |
| 5,053,212 A | 10/1991 | Constantz et al. | |
| 5,073,373 A | 12/1991 | O'Leary et al. | |
| 5,085,861 A | 2/1992 | Gerhart et al. | |
| 5,129,905 A | 7/1992 | Constantz | |
| 5,149,368 A | 9/1992 | Liu et al. | |
| 5,152,836 A | 10/1992 | Hirano et al. | |
| 5,178,845 A | 1/1993 | Constantz et al. | |
| 5,197,985 A | 3/1993 | Caplan et al. | |
| 5,226,914 A | 7/1993 | Caplan et al. | |
| 5,258,044 A | 11/1993 | Lee | |
| 5,262,166 A | 11/1993 | Liu et al. | |
| 5,281,265 A | 1/1994 | Liu | |
| 5,286,763 A | 2/1994 | Gerhart et al. | |
| 5,290,558 A | 3/1994 | O'Leary et al. | |
| 5,306,305 A | 4/1994 | Lee | |
| 5,336,264 A | 8/1994 | Constantz et al. | |
| 5,342,441 A | 8/1994 | Mandai et al. | |
| 5,352,715 A | 10/1994 | Wallace et al. | |
| 5,399,665 A | 3/1995 | Barrera et al. | |
| 5,443,832 A | 8/1995 | Amerongen et al. | |
| 5,462,751 A | 10/1995 | Kossovsky et al. | |
| 5,470,803 A | 11/1995 | Bonfield et al. | |

(Continued)

FOREIGN PATENT DOCUMENTS

| | | |
|---|---|---|
| CN | 1297042 | 5/2001 |
| EP | 0 268 463 | 5/1988 |

(Continued)

OTHER PUBLICATIONS

Aggerbeck and Heron, "Adjuvanticity of Aluminum Hydroxide and Calcium Phosphate in Diphtheria-Tetanus Vaccines I," *Vaccine* 13:1360-1365 (1995).

(Continued)

*Primary Examiner* — Aradhana Sasan
(74) *Attorney, Agent, or Firm* — Clark & Elbing LLP; Todd Armstrong

(57) ABSTRACT

Porous calcium phosphate implant compositions that approximate the chemical composition of natural bone mineral are provided. In addition to calcium phosphate, the compositions include an effervescent agent to promote the formation of interconnected pores and a cohesiveness agent to maintain the shape and hardness of the hardened composition. When introduced at an implant site, the calcium phosphate compositions are remodeled into bone. Methods for using the calcium phosphate compositions, e.g., to repair or replace bone, are also provided.

29 Claims, 1 Drawing Sheet

(56) References Cited

U.S. PATENT DOCUMENTS

| | | | |
|---|---|---|---|
| 5,486,359 A | 1/1996 | Caplan et al. | |
| 5,496,399 A | 3/1996 | Ison et al. | |
| 5,508,342 A | 4/1996 | Antonucci et al. | |
| 5,510,396 A | 4/1996 | Prewett et al. | |
| 5,514,378 A | 5/1996 | Mikos et al. | |
| 5,516,532 A | 5/1996 | Atala et al. | |
| 5,522,893 A | 6/1996 | Chow et al. | |
| 5,525,148 A | 6/1996 | Chow et al. | |
| 5,542,973 A | 8/1996 | Chow et al. | |
| 5,543,019 A | 8/1996 | Lee et al. | |
| 5,545,254 A | 8/1996 | Chow et al. | |
| 5,565,502 A | 10/1996 | Glimcher et al. | |
| 5,569,442 A | 10/1996 | Fulmer et al. | |
| 5,571,493 A | 11/1996 | Fulmer et al. | |
| 5,580,623 A | 12/1996 | Fulmer et al. | |
| 5,605,713 A | 2/1997 | Boltong | |
| 5,650,176 A | 7/1997 | Lee et al. | |
| 5,665,120 A | 9/1997 | Ohtsuka et al. | |
| 5,676,976 A | 10/1997 | Lee et al. | |
| 5,683,461 A | 11/1997 | Lee et al. | |
| 5,683,496 A | 11/1997 | Ison et al. | |
| 5,683,667 A | 11/1997 | Fulmer et al. | |
| 5,691,397 A | 11/1997 | Glimcher et al. | |
| 5,697,981 A | 12/1997 | Ison et al. | |
| 5,700,289 A | 12/1997 | Breitbart et al. | |
| 5,702,717 A | 12/1997 | Cha et al. | |
| 5,709,742 A | 1/1998 | Fulmer et al. | |
| 5,763,092 A | 6/1998 | Lee et al. | |
| 5,782,971 A | 7/1998 | Constantz et al. | |
| 5,783,217 A | 7/1998 | Lee et al. | |
| 5,795,330 A | 8/1998 | Tofighi et al. | |
| 5,820,632 A | 10/1998 | Constantz et al. | |
| 5,843,289 A | 12/1998 | Lee et al. | |
| 5,846,312 A | 12/1998 | Ison et al. | |
| 5,885,540 A | 3/1999 | Fulmer et al. | |
| 5,900,254 A | 5/1999 | Constantz | |
| 5,904,716 A | 5/1999 | Gendler | |
| 5,952,010 A | 9/1999 | Constantz | |
| 5,958,504 A | 9/1999 | Lee et al. | |
| 5,962,028 A | 10/1999 | Constantz | |
| 5,964,932 A | 10/1999 | Ison et al. | |
| 5,968,253 A | 10/1999 | Poser et al. | |
| 5,980,482 A | 11/1999 | Tofighi et al. | |
| 6,002,065 A | 12/1999 | Constantz et al. | |
| 6,005,162 A | 12/1999 | Constantz | |
| 6,027,742 A * | 2/2000 | Lee et al. | 424/422 |
| 6,030,635 A | 2/2000 | Gertzman et al. | |
| 6,033,582 A | 3/2000 | Lee et al. | |
| 6,053,970 A | 4/2000 | Ison et al. | |
| 6,071,982 A | 6/2000 | Wise et al. | |
| 6,117,456 A | 9/2000 | Lee et al. | |
| 6,132,463 A | 10/2000 | Lee et al. | |
| 6,139,578 A | 10/2000 | Lee et al. | |
| 6,214,368 B1 | 4/2001 | Lee et al. | |
| 6,277,151 B1 | 8/2001 | Lee et al. | |
| 6,287,341 B1 | 9/2001 | Lee et al. | |
| 6,331,312 B1 | 12/2001 | Lee et al. | |
| 6,334,891 B1 | 1/2002 | Constantz et al. | |
| 6,340,477 B1 | 1/2002 | Anderson | |
| 6,443,988 B2 | 9/2002 | Felt et al. | |
| 6,461,631 B1 | 10/2002 | Dunn et al. | |
| 6,464,889 B1 | 10/2002 | Lee et al. | |
| 6,541,037 B1 | 4/2003 | Lee et al. | |
| 6,544,290 B1 | 4/2003 | Lee et al. | |
| 6,582,470 B1 | 6/2003 | Lee et al. | |
| 6,599,516 B1 | 7/2003 | Knaack | |
| 6,840,961 B2 | 1/2005 | Tofighi et al. | |
| 6,953,594 B2 | 10/2005 | Lee et al. | |
| 6,972,130 B1 | 12/2005 | Lee et al. | |
| 8,147,860 B2 * | 4/2012 | Rosenberg et al. | 424/423 |
| 2002/0076429 A1 | 6/2002 | Wironen et al. | |
| 2002/0098222 A1 | 7/2002 | Wironen et al. | |
| 2002/0155137 A1 | 10/2002 | Lee et al. | |
| 2002/0155167 A1 | 10/2002 | Lee et al. | |
| 2002/0187104 A1 * | 12/2002 | Li et al. | 424/44 |
| 2003/0120351 A1 | 6/2003 | Tofighi et al. | |
| 2003/0180344 A1 | 9/2003 | Wise et al. | |
| 2004/0002558 A1 | 1/2004 | McKay | |
| 2004/0097612 A1 | 5/2004 | Rosenberg et al. | |
| 2005/0084542 A1 | 4/2005 | Rosenberg et al. | |
| 2005/0106260 A1 | 5/2005 | Constantz et al. | |
| 2005/0147551 A1 | 7/2005 | Tofighi et al. | |
| 2005/0260278 A1 | 11/2005 | Constantz et al. | |
| 2005/0260279 A1 | 11/2005 | Constantz et al. | |
| 2006/0018974 A1 | 1/2006 | Constantz et al. | |

FOREIGN PATENT DOCUMENTS

| | | |
|---|---|---|
| EP | 0 347 028 | 12/1989 |
| EP | 0 419 275 | 3/1991 |
| EP | 0 664 133 | 7/1995 |
| JP | 63111875 | 5/1988 |
| JP | 63170205 | 7/1988 |
| JP | 2182261 | 7/1990 |
| JP | 5305134 | 11/1993 |
| JP | 6228011 | 8/1994 |
| JP | 7277712 | 10/1995 |
| JP | 2005512757 | 5/2005 |
| WO | WO 92/00109 | 1/1992 |
| WO | WO 92/02453 | 2/1992 |
| WO | WO 94/02412 | 2/1994 |
| WO | WO 94/04657 | 3/1994 |
| WO | WO 94/08458 | 4/1994 |
| WO | WO 94/20064 | 9/1994 |
| WO | WO 94/25080 | 11/1994 |
| WO | WO 95/08319 | 3/1995 |
| WO | WO 96/03160 | 2/1996 |
| WO | WO 96/36562 | 11/1996 |
| WO | WO 97/17285 | 5/1997 |
| WO | WO 98/16209 | 4/1998 |
| WO | WO 99/38543 | 8/1999 |
| WO | WO 01/08714 | 2/2001 |
| WO | WO 02/36518 | 5/2002 |
| WO | WO 02/100331 | 12/2002 |
| WO | WO 03/005137 A2 * | 7/2003 |
| WO | WO 03/057086 | 7/2003 |
| WO | WO 03/057137 | 7/2003 |
| WO | WO 2004/091435 | 10/2004 |

OTHER PUBLICATIONS

Alper et al., "Osteogenesis in Bone Defects in Rats: The Effects of Hydroxyapatite and Demineralized Bone Matrix," *Am. J. Med. Sci.* 298:371-376 (1989).

Aoki, "Science and Medical Applications of Hydroxyapatite," *JAAS* 11-15 (1991).

Appel et al., "Recent Advances in Implants for Bone Growth Promotion," *Exp. Opin. Ther. Patents* 4:1461-1469 (1994).

Atala et al., "Injectable Alginate Seeded with Chondrocytes as a Potential Treatment for Vesicoureteral Reflux," *J. Urol.* 150:745-747 (1993).

Athanasou, "Cellular Biology of Bone-Resorbing Cells," *J. Bone Joint Surg. Am.* 78:1096-1112 (1996).

Attawia et al., "Osteoblast-Like Cell Adherence and Migration Through 3-Dimensional Porous Polymer Matrices," *Biochem. Biophys. Res. Commun.* 213:639-644 (1995).

Barton et al., "Surface and Bulk Properties of Amorphous Calcium Phosphate," *Surface Chem. Colloids* 87:379 No. 73954v (1977).

Benghuzzi et al., "Alcap Ceramic Implantable Devices and the Effect of Surface Area on the Delivery of Various Steroid Hormones," 8th Southern Biomedical Engineering Conference, Richmond, VA, Oct. 15-16, 1989; *Biomater. Artif. Cells Artif. Organs*, 17:463 (1989).

Benghuzzi et al., "Long-Term Delivery of Danazol by Biodegradable Ceramic Devices," 8th Southern Biomedical Engineering Conference, Richmond, VA, Oct. 15-16, 1989; *Biomater. Artif. Cells Artif. Organs*, 17:463 (1989).

Benghuzzi et al., "Resorbable and Biodegradable Ceramics as Drug Delivery Systems," 8th Southern Biomedical Engineering Conference, Richmond, VA, Oct. 15-16, 1989; *Biomater. Artif. Cells. Artif. Organs*, 17:463 (1989).

Benghuzzi et al., "Controlled Release of Hydrophilic Compounds by Resorbable and Biodegradable Ceramic Drug Delivery Devices," *Biomed. Sci. Instrum.* 28:179-182 (1992).

Besic et al., "Electron Probe Microanalysis of Noncarious Enamel and Dentin and Calcified Tissues in Mottled Teeth," *J. Dent. Res.* 48:131-139 (1969).

Bonfield, "Chapter 16—Design of Bioactive Ceramic-Polymer Composites," An Introduction to Bioceramics, IRC in Biomedical Materials, Queen Mary and Westfield College, London, UK, 16:299-303 (1993).

Boskey, "Matrix Proteins and Mineralization: An Overview," *Connect. Tissue Res.* 35:357-363 (1996).

Brown, "Phase Relationships in the Ternary System $CaO-P_2O_5-H_2O$ at 25° C.," *J. Am. Ceram. Soc.* 75:17-22 (1992).

Cannon et al., "Continuous Delivery of Azidothymidine by Hydroxyapatite or Tricalcium Phosphate Ceramics," *Biomed. Sci. Instrum.* 31:159-164 (1995).

Chung et al., "Biological Effects of Drug-Loaded Biodegradable Membranes for Guided Bone Regeneration," *J. Periodont. Res.* 32:172-175 (1997).

Constantz et al., "Skeletal Repair by in Situ Formation of the Mineral Phase of Bone," *Science* 267:1796-1799 (1995).

Covey et al., "Clinical Induction of Bone Repair with Demineralized Bone Matrix or a Bone Morphogenetic Protein," *Orthop. Rev.* 18:857-863 (1989).

Denissen et al., "Net-Shaped Hydroxyapatite Implants for Release of Agents Modulating Periodontal-Like Tissues," *J. Periodontal Res.* 32:40-46 (1997).

Driessens et al., "Calcium Phosphate Bone Cements," *Encyc. Hand. Biomat. Bioeng.*, pp. 855-877 (1995).

Ducheyne et al., "Chapter 15: Bioceramic Composites," *Advanced Series in Ceramics-vol. 1: An Introduction to Bioceramics* 281-297 (1993).

Eanes et al., "Intermediate States in the Precipitation of Hydroxyapatite," *Nature* 208:365-367 (1965).

Eanes et al., "Intermediate Phases in the Basic Solution Preparation of Alkaline Earth Phosphates," *Chemical Abstracts* 69:10348, No. 110373f (1968).

Eanes, "Thermochemical Studies on Amorphous Calcium Phosphate," *Calcif. Tissue Res.* 5:133-145 (1970).

Elgendy et al., "Osteoblast-Like Cell (MC3T3-E1) Proliferation on Bioerodible Polymers: An Approach Towards the Development of a Bone-BioErodible Polymer Composite Material," *Biomater.* 14:263-269 (1993).

Fabbri et al., "Hydroxyapatite-Based Porous Aggregates: Physico-Chemical Nature, Structure, Texture and Architecture," *Biomater.* 16: 225-228 (1995).

Fink and Simonsmeier, "Business Laws," *Rem. Pharm. Sci. 17th Ed.*, pp. 1890-1891 (1985).

Freed et al., "Cultivation of Cell-Polymer Cartilage Implants in Bioreactors," *J. Cellular Biochemistry* 51:257-264 (1993).

Freed et al., "Biodegradable Polymer Scaffolds for Tissue Engineering," Biotech. 12:689-693 (1994).

Gennaro, ed., "Clinical/ Medical Testing," *Rem. Pharm. Sci. 17th Ed.*, pp. 39-40 (1985).

Glimcher et al., "Recent Studies of Bone Mineral: Is the Amorphous Calcium Phosphate Theory Valid," *J. Crystal Growth* 53:100-119 (1981).

Glimcher, "Recent Studies of the Mineral Phase in Bone and its Possible Linkage to the Organic Matrix by Protein-Bound Phosphate Bonds," *Philos. Trans. R. Soc. Lond. B.* 304:479-508 (1984).

Glowacki et al., "Demineralized Bone Implants," *Clin. Plast. Surg.* 12:233-241 (1985).

Goto et al., "Studies on the Toxicities of Aluminum Hydroxide and Calcium Phosphate as Immunological Adjuvants for Vaccines," *Vaccine* 11:914-918 (1993).

Goto et al., "Local Tissue Irritating Effects and Adjuvant Activities of Calcium Phosphate and Aluminum Hydroxide with Different Physical Properties," *Vaccine* 15:1364-1371 (1997).

Graves et al., "Resorbable Ceramic Implants," *J. Biomed. Mater. Res. Symposium* 2:91-115 (1971).

Greenfield et al., "Formation Chemistry of Amorphous Calcium Phosphates Prepared from Carbonate Containing Solutions," *Calc. Tiss. Res.* 9:152-162 (1972).

Gupta et al., "Adjuvants—A Balance Between Toxicity and Adjuvanticity," *Vaccine* 11:293-306 (1993).

Gupta et al., "Comparison of Adjuvant Activities of Aluminum Phosphate, Calcium Phosphate and Stearyl Tyrosine for Tetanus Toxoid," *Biologicals* 22:53-63 (1994).

Hirasawa et al., "Manufacture of High Purity Hydroxyapatite," *Chemical Abstracts* 108:166-167, No. 78193h (1988).

Holmes et al., "Surface Areas by Gas Adsorption on Amorphous Calcium Phosphate and Crystalline Hydroxyapatite," *Calc. Tiss. Res.* 7:163-174 (1971).

Hubbell, "Biomaterials in Tissue Engineering," *Biotech.* 13:565-576 (1995).

Ickovic et al., "Calcium-Phosphate-Adjuvanted Allergens: Total and Specific IgE Levels Before and After Immunotherapy with House Dust and *Dermatophagoides pteronyssinus* Extracts," *Ann. Immunol.* 134D:385-398 (1983).

Ijntema et al., "Hydroxyapatite Microcarriers for Biocontrolled Release of Protein Drugs," *Int'l. J. Pharm.* 112:215-224 (1994).

Ikada et al., "Release of Antibiotic from Composites of Hydroxyapatite and Poly(lactic acid)," *J. Control. Release* 2:179-186 (1985).

Ishaug et al., "Osteoblast Function on Synthetic Biodegradable Polymers," *J. Biomed. Mater. Res.* 28:1445-1453 (1994).

Ishikawa et al., "Effects of Preparation Conditions in Aqueous Solution on Properties of Hydroxyapatites," *Chemical Abstracts* 113: 6001, No. 218168 (1990).

Itokazu et al., "Drug Delivery Systems Using Porous Hydroxyapatite Blocks," *J. Orthop. Surg.* 2:47-50 (1994).

Kato et al., "Relationship Between Hemolytic Activity and Adsorption Capacity of Aluminum Hydroxide and Calcium Phosphate as Immunological Adjuvants for Biologicals," *Microbiol. Immunol.* 38:543-548 (1994).

Knaack et al., "Novel Fully Resorbable Calcium Phosphate Bone Substitute," *1997 ASBMR Abstract* 12: s202, (1997).

Knaack, "Endothermically Setting Calcium Phosphate Bone Substitute," Orthopaedic Congress, Aug. 20-22, 1997, Boston, MA.

Knaack et al., "A Fully Resorbable Calcium Phosphate Bone Substitute," Portland Bone Symposium, pp. 692-701 (1997).

Kossovsky et al., "Surface-Modified Nanocrystalline Ceramics for Drug Delivery Applications," *Biomaterials* 15:1201-1207 (1994).

Kossovsky et al., "Preservation of Surface-Dependent Properties of Viral Antigens Following Immobilization on Particulate Ceramic Delivery Vehicles," *J. Biomed. Mat. Res.* 29:561-573 (1995).

Kreuter et al., "Influence of the Particle Size on the Adjuvant Effect of Particulate Polymeric Adjuvants," *Vaccine* 4:125-129 (1986).

Labarthe et al., "Sur la Structure et les Propriétés des Apatites Carbonatées de Type B Phospho-Calciques," *Ann. Chem.* 8:289-301 (1973), Summary only.

Mileti et al., "Development of a Hydroxyapatite Ceramic Matrix for the Continuous Delivery of Coumadin," *Biomed. Sci. Instrum.* 31:177-182 (1995).

Moldovan et al., "A Ceramic System for Continuous Release of Acetylsalicylic Acid," *Biomed. Sci. Instrum.* 30:175-180 (1994).

Moldovan et al., "Continuous Delivery of Analgesics by Ceramics," Fifth World Biomaterials Congress, Toronto, Canada, Jun. 2, 1996 (Abstract only).

Norian Corporation, Product Information Sheet, "The Material Science of Norian SRS™, Skeletal Repair System™," (1997).

Nylen et al., "Molecular and Ultrastructural Studies of Non-Crystalline Calcium Phosphates," *Calcif. Tissue Res.* 9:95-108 (1972).

Otsuka et al., "Drug Release Behavior from Self-Setting Calcium Phosphate Cement Containing Anti-Cancer Drug," *Proceed. Intern. Symp. Control. Rel. Bioact. Mater.* 21:268-269 (1994).

Otsuka et al., "A Novel Skeletal Drug Delivery System Using Self-Setting Calcium Phosphate Cement. 4: Effects of the Mixing Solution Volume on the Drug Release Rate of Heterogenous Aspirin-Loaded Cement," *J. Pharm. Sci.* 83:259-263 (1994).

Otsuka et al., "A Novel Skeletal Drug Delivery System Using Self-Setting Calcium Phosphate Cement. 9: Effects of the Mixing Solution Volume on Anticancer Drug Release from Homogeneous Drug-Loaded Cement," *J. Pharm. Sci.* 84:733-736 (1995).

Otsuka et al., "Effect of Particle Size of Metastable Calcium Phosphates on Mechanical Strength of a Novel Self-Setting Bioactive Calcium Phosphate Cement," *J. Biomed. Mater. Res.* 29:25-32 (1995).

Pool, "Coral Chemistry Leads to Human Bone Repair," *Science* 267:1772 (1995).

Posner et al., "Synthetic Amorphous Calcium Phosphate and its Relation to Bone Mineral Structure," *Bone Mineral Structure* 8:273-281 (1975).

Redondo et al., "Effect of particulate porous hydroxyapatite on osteoinduction of demineralized bone autografts in experimental reconstruction of the rat mandible," *Int. J. Oral. Maxillofar. Surg.* 24:445-448 (1995).

Relyveld, "Current Developments in Production and Testing of Tetanus and Diptheria Vaccines," *New Developments with Human and Veterinary Vaccines*, pp. 51-76 (1980).

Relyveld et al., "Calcium Phosphate Adjuvanted Allergens," *Annals of Allergy* 54:521-529 (1985).

Relyveld et al., "Preparation and Use of Calcium Phosphate Adsorbed Vaccines," *Develop. Biol. Standard* 65:131-136 (1986).

Relyveld et al, "Humoral Response in Rabbits Immunized with Calcium Phosphate Adjuvanted HIV-1 gp160 Antigen," *Biomed. & Pharmacother*. 48:79-83 (1994).

Rey et al., "The Carbonate Environment in Bone Mineral: A Resolution-Enhanced Fourier Transform Infrared Spectroscopy Study," *Calcif. Tissue Int.* 45:157-164 (1989).

Rey et al., "Structural Studies of the Mineral Phase of Calcifying Cartilage," *J. Bone Miner. Res.* 6:515-525 (1991).

Rey et al., "Preparation of Microporous Ceramic at Low Temperature from Poorly Crystalline Apatite," *Symposium V: Hydroxyapatite and related compounds* (1993) (Abstract only).

Rey et al., "Chemical Properties of Poorly Crystalline Apatites" *Phosphorus Res. Bull.* 6:67-70 (1996) (Abstract only).

Shinto et al., "Calcium Hydroxyapatite Ceramic Used as a Delivery System for Antibiotics," *J. Bone Joint Surg. Br.* 74-B:600-604 (1992).

Shors et al., "Chapter 10: Porous Hydroxyapatite," In *An Introduction to Bioceramics*, eds. Hersch et al., Work Sci. Publ. Co. Pte. Ltd.: 181-198 (1993).

Termine et al., "Amorphous/Crystalline Interrelationships in Bone Mineral," *Calc. Tissue Res.* 1:8-23 (1967).

Thoma et al., "Biodegradable Gentamicin Depot-Implants Made of Beta-Tricalcium Phosphate Ceramics. 3: In Vivo Studies on Drug Release, Tissue Tolerance, and Biodegradation," *Pharmazie* 46:266-270 (1991) (Abstract only).

Thoma et al., "Biodegradable Controlled Release Implants Based on β-Tricalcium Phosphate Ceramic," *Eur. J. Pharm. Biopharm.* 38:107-112 (1992).

Thomson et al., "Fabrication of Biodegradable Polymer Scaffolds to Engineer Trabecular Bone," *J. Biomater. Sci. Polym. Edn.* 7:23-30 (1995).

Törmälä, "Biodegradable Self-Reinforced Composite Materials; Manufacturing Structure and Mechanical Properties," *Clin. Mater.* 10:29-34 (1992).

Tung et al., "An Intermediate State in Hydrolysis of Amorphous Calcium Phosphate," *Calcif. Tissue Int.* 35:783-790 (1983).

Tung, "In Vitro Drug Release of Antibiotic-Loaded Porous Hydroxyapatite Cement," *Artif. Cells Blood Substit. Immob. Biotech.* 23:81-88 (1995).

Uchida et al., "Slow Release of Anticancer Drugs from Porous Calcium Hydroxyapatite Ceramic," *J. Orthop. Res.* 10:440-445 (1992).

Vassilev, "Aluminium Phosphate But Not Calcium Phosphate Stimulates the Specific IgE Response in Guinea Pigs to Tetanus Toxoid," *Allergy* 33:155-159 (1978).

Yamamura et al., "Antitumor Effects and Distributions of Adriamycin Incorporated Into Hydroxyapatite Implants in a Cancer Rat Model Bearing Swarm Rat Chondrosarcoma," *Japan. J. Pharm.* 66:433-438 (1994).

Yamamura et al., "Anticancer Effects of Adriamycin-Loaded Hydroxyapatite Implants Determined in a Swarm Rat Chondrosarcoma Model," *Japan. J. Pharm.* 65:289-291 (1994).

Yasue et al., "Effect of Adsorption of Succinic Acid on the Formation of Amorphous Calcium Phosphate," *J. Ceramic Soc. Japan* (International Edition) 102:1125-1130 (1994).

European Office Communication, dated Jan. 10, 2012, in EP 06 844 849.7-1219.

Extended European Search Report mailed on Sep. 30, 2010 in European Application No. 06844849.7.

Office Action mailed Jun. 26, 2012, in Japanese Patent Application No. 2008-544447.

Office Communication, dated Jul. 5, 2012, in European Patent Application No. 06844849.7.

Office Action dated, Jun. 20, 2012, in Chinese Patent Application No. 200680052052.7.

Second Office Action, dated Jan. 25, 2011, in Chinese Patent Application No. 200680052052.7 (Original in Chinese; English Translation Provided).

* cited by examiner

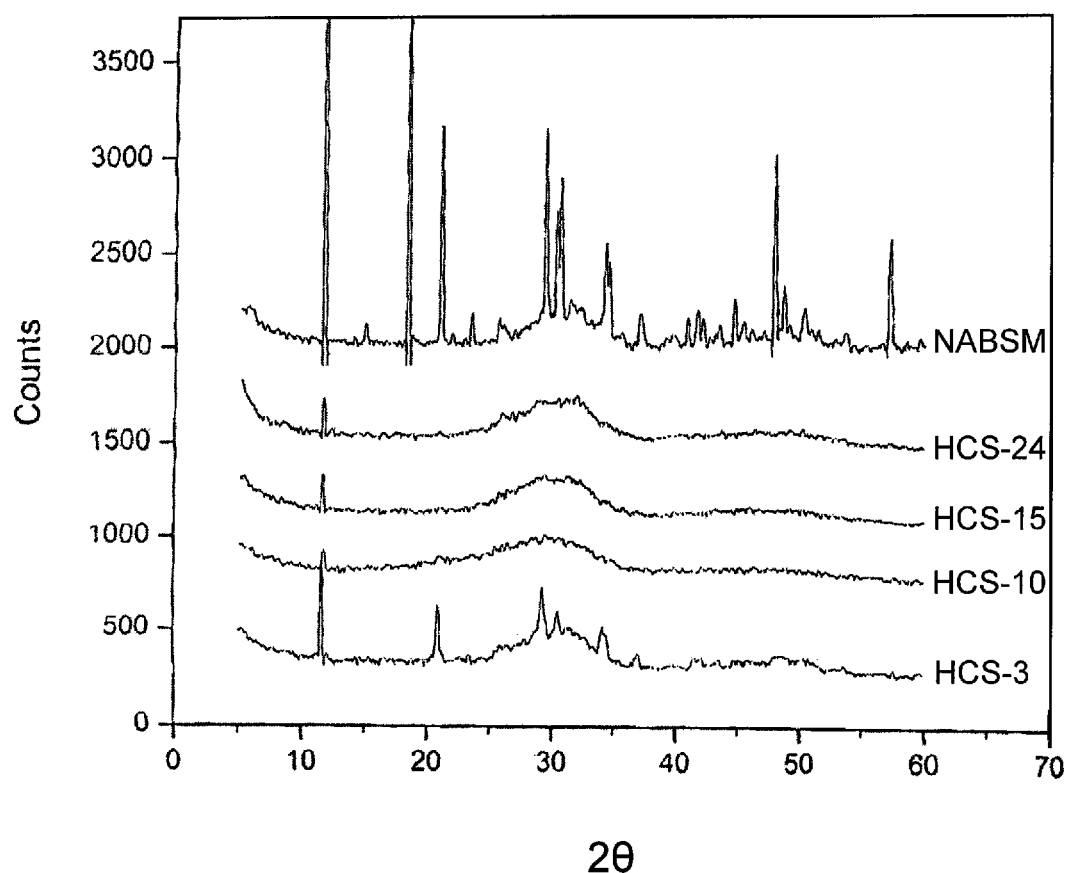

POROUS CALCIUM PHOSPHATE BONE MATERIAL

CROSS REFERENCE TO RELATED APPLICATIONS

This application is a continuation of U.S. patent application Ser. No. 11/294,819, filed on Dec. 6, 2005, which is hereby incorporated by reference in its entirety.

BACKGROUND OF THE INVENTION

The field of the present invention is bone repair and replacement. More specifically, the invention relates to a self-hardening, porous calcium phosphate composition, which has desirable handling characteristics and mechanical properties.

Naturally-occurring bone is comprised of both organic and inorganic components. The organic component includes growth factors, cartilage, collagen, and other proteins. The inorganic bone component includes non-stoichiometric, poorly crystalline apatitic (PCA) calcium phosphate, having a Ca/P ratio between 1.45 and 1.75 (Besic et al. (1969) *J. Dental Res.* 48(1):131). This inorganic bone mineral is continuously resorbed and regenerated in vivo by osteoclasts and osteoblasts in a process known as remodeling.

Bone implants are often used to augment the natural regeneration process in the event of bone defects and injuries. These implants must be biocompatible, capable of manipulation by a surgeon prior to implantation, and of a strength and composition such that the implant will maintain its shape in vivo.

Given its regenerative capabilities, natural bone is a potential implant material. However, the use of autogenic, allogenic, and xenogeneic bone is complicated by associated disease transmission, immunogenic implant rejection, patient morbidity, and complicated surgical procedures. Thus, synthetic bone implant materials have become the focus of increasing attention.

Moldable, self-setting calcium phosphate cements exhibit good strength properties and can be easily formed in situ to fill a range of clinical defects, but are remodeled slowly because cells cannot penetrate the dense material. Porous calcium phosphate ceramics are preferred as an implant material because they allow the penetration of blood vessels, cells and tissues, and drugs, which are important for promoting bone formation and preventing infection. When used as an implant material, porous calcium phosphate ceramics preferably have a high porosity. This high porosity can lead to lower mechanical strength in the porous bodies, thus negating their benefit as bone implants, which require high mechanical strength. Additionally, preformed porous blocks and granules can be difficult to manipulate and implant, and can lead to incomplete defect fill. Thus, there is a need for porous calcium phosphate ceramics having both excellent biocompatibility and mechanical strength.

SUMMARY OF THE INVENTION

Self-hardening, porous calcium phosphate compositions are provided that approximate the chemical composition of natural bone. The porosity (number and size of pores) of the calcium phosphate composition is determined by the rate of release of a gaseous component of an effervescent agent, which escapes from the mixture during the hardening process.

In a first aspect, the invention features a composition that includes a calcium phosphate, an effervescent agent, and a biocompatible cohesiveness agent (e.g., a binder). The composition is prepared using a calcium phosphate source selected from amorphous calcium phosphate, poorly crystalline calcium phosphate, hydroxyapatite, carbonated apatite (calcium-deficient hydroxyapatite), monocalcium phosphate, calcium metaphosphate, heptacalcium phosphate, dicalcium phosphate dihydrate, tetracalcium phosphate, octacalcium phosphate, calcium pyrophosphate, and tricalcium phosphate, or mixtures thereof. Alternatively, the composition is prepared using an amorphous calcium phosphate and a second calcium phosphate source, e.g., poorly crystalline calcium phosphate, hydroxyapatite, carbonated apatite (calcium-deficient hydroxyapatite), monocalcium phosphate, calcium metaphosphate, heptacalcium phosphate, dicalcium phosphate dihydrate, tetracalcium phosphate, octacalcium phosphate, calcium pyrophosphate, or tricalcium phosphate, or mixtures thereof.

In an embodiment, the effervescent agent includes a carbonate/bicarbonate mixture, in which the carbonate and bicarbonate components are combined in a predetermined molar ratio, e.g., a ratio in the range of about 1:1 to about 1:9 carbonate/bicarbonate, preferably in the range of about 1:1, 1:2, 1:3, 1:4, 1:5, 1:6, 1:7, 1:8, or 1:9. In an embodiment, the effervescent agent is a mixture of carbonate/bicarbonate compounds having the formula $M_xCO_3/M'_yCO_3$, in which M and M' are monovalent cations, e.g., sodium (Na), potassium (K), lithium (Li), rubidium (Rb), cesium (Cs), silver (Ag), thallium (Tl), and ammonium ($NH_4^+$), x=2, and y=1. In another embodiment, the effervescent agent is a mixture of carbonate/bicarbonate compounds having the formula $M_xCO_3/M'_yCO_3$, in which M is a divalent cation, e.g., barium (Ba), cadmium (Cd), calcium (Ca), cobalt (Co), copper (Cu), iron (Fe), magnesium (Mg), manganese (Mn), nickel (Ni), strontium (Sr), and zinc (Zn), M' is a monovalent cation, e.g., sodium (Na), potassium (K), lithium (Li), rubidium (Rb), cesium (Cs), silver (Ag), thallium (Tl), and ammonium ($NH_4^+$), x=1, and y=1. In a preferred embodiment, the molar ratio of carbonate to bicarbonate in the effervescent agent is selected to promote the controlled release of carbon dioxide from the calcium phosphate composition as it hardens. In another embodiment, the molar ratio of the carbonate/bicarbonate components of the effervescent agent is selected to promote the formation of interconnected pores exhibiting a median pore size of about 1 to about 1000 μm in diameter, more preferably about 10 to about 100 μm in diameter. In yet another embodiment, pore formation is promoted by the release of carbon dioxide from the effervescent agent for at least one minute, more preferably at least 2, 3, or 4 minutes, and most preferably for about 5 minutes or more; an increase in the molar ratio of bicarbonate relative to the molar ratio of carbonate in the effervescent agent increases the time of release of carbon dioxide with a concomitant increase in porosity.

In another embodiment, the effervescent agent is a gas that is dissolved in the calcium phosphate composition prior to implantation, and that is released from the calcium phosphate composition during hardening at a rate selected to produce a desired amount of interconnected pores. For example, the effervescent agent is selected for its ability to release a gas for 1 minute, preferably 2, 3, or 4 minutes, and more preferably for about 5 or more minutes during the hardening process so as to produce a hardened calcium phosphate having at least about 5% to 60% porosity. Preferably the calcium phosphate composition has a porosity of about 5%, more preferably about 10, 20, or 30% porosity, and most preferably about 40, 50, or 60% porosity. In a preferred embodiment, the calcium phosphate has at least about 50% porosity. Preferably, the effervescent agent is selected to promote the formation of interconnected pores exhibiting a median pore size of about 1 to about 1000 μm in diameter, more preferably about 10 to about 100 μm in diameter. In preferred embodiments, the gas is selected from carbon dioxide, air, nitrogen, helium, oxygen, and argon. In another embodiment, the effervescent agent is a solid material which liberates gas upon dissolution (e.g., a carbonate, such as sodium bicarbonate). In a preferred embodiment, the effervescent agent produces a continuous matrix of interconnected porosity during hardening of the calcium phosphate composition. In another preferred embodiment, the effervescent agent is present in an amount in the range of about 1 to about 40 wt %. In another embodiment, the effervescent agent is selected for its ability to effervesce slowly at biological temperatures, preferably in the range of between about 4° C. and 42° C., more preferably in the range of between about 15° C. and 37° C., and most preferably at about 37° C.

In other embodiments, the amorphous calcium phosphate and the second calcium phosphate source have an average crystalline domain size of less than 100 nm (e.g., in the range of between about 1 nm to about 99 nm; preferably 50 nm or less; more preferably 10 nm or less).

In another embodiment, the calcium phosphate is an amorphicized calcium phosphate, which has, e.g., an average crystalline domain size of less than about 100 nm and a tap density of greater than 0.7 g/cm$^3$. In another embodiment, the amorphicized calcium phosphate is selected from one or more of amorphous calcium phosphate, poorly crystalline calcium phosphate, hydroxyapatite, carbonated apatite (calcium-deficient hydroxyapatite), monocalcium phosphate, calcium metaphosphate, heptacalcium phosphate, dicalcium phosphate dihydrate, tetracalcium phosphate, octacalcium phosphate, calcium pyrophosphate, and tricalcium phosphate, or mixtures thereof.

In another embodiment, the composition includes a biocompatible cohesiveness agent. In preferred embodiments, the cohesiveness agent includes polymers selected from polysaccharides, nucleic acids, carbohydrates, proteins, polypeptides, poly(α-hydroxy acids), poly(lactones), poly(amino acids), poly(anhydrides), poly(orthoesters), poly(anhydride-co-imides), poly(orthocarbonates), poly(α-hydroxy alkanoates), poly(dioxanones), poly(phosphoesters), poly(L-lactide) (PLLA), poly(D,L-lactide) (PDLLA), polyglycolide (PGA), poly(lactide-co-glycolide (PLGA), poly(L-lactide-co-D, L-lactide), poly(D,L-lactide-co-trimethylene carbonate), polyhydroxybutyrate (PHB), poly(ϵ-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly(ethylene terephthalate)polyamide, and copolymers thereof. Preferred cohesiveness agents also include alginic acid, arabic gum, guar gum, xantham gum, gelatin, chitin, chitosan, chitosan acetate, chitosan lactate, chondroitin sulfate, N,O-carboxymethyl chitosan, a dextran (e.g., α-cyclodextrin, β-cyclodextrin, γ-cyclodextrin, or sodium dextran sulfate), fibrin glue, glycerol, hyaluronic acid, sodium hyaluronate, a cellulose (e.g., methylcellulose, carboxy methylcellulose, hydroxypropyl methylcellulose, or hydroxyethyl cellulose), a glucosamine, a proteoglycan, a starch (e.g., hydroxyethyl starch or starch soluble), lactic acid, a pluronic, sodium glycerophosphate, collagen, glycogen, a keratin, silk, and mixtures thereof. In yet another preferred embodiment, the biocompatible cohesiveness agent is present in the composition in an amount in the range of about 0.5 wt % to about 20 wt % (e.g., less than about 20 wt %, preferably less than about 10 wt %, more preferably less than about 5 wt %, and most preferably less than about 1 wt %).

In other embodiments, the physiologically-acceptable fluid, when added to the dry components of the composition, produces a self-hardening paste or putty. In several embodiments of the invention, suitable physiologically-acceptable fluids include but are not limited to water, saline, and phosphate buffers. In other embodiments, the fluid can be a biological fluid, e.g., any treated or untreated fluid (including a suspension) associated with living organisms, particularly blood, including whole blood, warm or cold blood, and stored or fresh blood; treated blood, such as blood diluted with at least one physiological solution, including but not limited to saline, nutrient, and/or anticoagulant solutions; blood components, such as platelet concentrate (PC), apheresed platelets, platelet-rich plasma (PRP), platelet-poor plasma (PPP), platelet-free plasma, plasma, serum, fresh frozen plasma (FFP), components obtained from plasma, packed red cells (PRC), buffy coat (BC); blood products derived from blood or a blood component or derived from bone marrow; red cells separated from plasma and resuspended in physiological fluid; and platelets separated from plasma and resuspended in physiological fluid. In yet other embodiments, the biological fluid includes, e.g., milk, urine, saliva, seminal or vaginal fluid, synovial fluid, lymph fluid, amniotic fluid, the fluid within the yolk sac, the chorion, or the allantois of an egg, sweat, and tears.

The calcium phosphate compositions of the invention, once hydrated to form a paste, have improved flow characteristics compared to most previously-known bone implant materials. Varying amounts of fluid may be added to the powder to produce a paste having the desired characteristics. For example, in at least some embodiments, 0.5-2.0 cc of fluid per gram of powder is used to prepare a paste that is formable, i.e., capable of being molded and retaining its shape. In at least some embodiments, the paste is injectable, i.e., capable of passing through a 16- to 18-gauge needle. The paste can also be prepared for delivery through a catheter (e.g., a catheter having a 7-15 gauge needle, and more preferably a 7, 8, 9, 10, 11, 12, 13, 14, or 15 gauge needle).

In another aspect, the composition, when hydrated, produces a formable, self-hardening, paste, which is moldable and cohesive when applied to an implant site in vivo, and hardens to form a porous calcium phosphate composition. In at least some embodiments, the paste hardens to form a calcium phosphate composition (e.g., a poorly crystalline apatitic (PCA) calcium phosphate) having significant compressive strength. The composition may be implanted in vivo in paste form or as hardened calcium phosphate. The composition can be used to repair bone, e.g., damaged bone, or as a delivery vehicle for biologically active agents.

According to some embodiments, the composition additionally includes a biologically active agent. Biologically active agents that can be used in the compositions and methods described herein include, without limitation, an antibody, an antibiotic, a polynucleotide, a polypeptide, a protein (e.g., an osteogenic protein), an anti-cancer agent, a growth factor, and a vaccine. Osteogenic proteins include, without limitation, BMP-2, BMP-3, BMP-3b, BMP-4, BMP-5, BMP-6, BMP-7, BMP-8, BMP-9, BMP-10, BMP-11, BMP-12, BMP-13, BMP-14, BMP-15, BMP-16, BMP-17, and BMP- 18. Anti-cancer agents include, without limitation, alkylating agents, platinum agents, antimetabolites, topoisomerase inhibitors, antitumor antibiotics, antimitotic agents, aromatase inhibitors, thymidylate synthase inhibitors, DNA antagonists, farnesyltransferase inhibitors, pump inhibitors, histone acetyltransferase inhibitors, metalloproteinase inhibitors, ribonucleoside reductase inhibitors, TNF alpha agonists, TNF alpha antagonists, endothelin A receptor antagonists, retinoic acid receptor agonists, immuno-modulators, hormonal agents, antihormonal agents, photodynamic agents, and tyrosine kinase inhibitors.

In another preferred embodiment, the composition includes demineralized bone matrix (DBM). In a preferred embodiment, the DBM has a particle size in the range of 53-850 μm. In other embodiments, the DBM has a particle size in the range of 53-125 μm (i.e., fines) or 125-850 μm (i.e., full range DBM particles).

In other embodiments, the calcium phosphate composition has a Ca/P ratio of less than 1.67. In particularly preferred embodiments, the formable, self-hardening, porous calcium phosphate paste hardens to form a calcium phosphate having an overall Ca/P ratio in the range of 1.0-1.67, preferably 1.3-1.65, more preferably 1.4-1.6, and most preferably close to that of naturally-occurring bone, that is in the range of 1.45 to 1.67. In a preferred embodiment, the calcium phosphate composition has a Ca/P ratio of equal to or less than about 1.5.

In yet other embodiments, the porous, hardened calcium phosphate composition exhibits a compressive strength of equal to or greater than about 1 or 2 MPa. In other preferred embodiments, the compressive strength is in the range of about 1 MPa to about 150 MPa (e.g., 20, 30, 40, 50, 60, 70, 80, 90, or 100 MPa). In yet other preferred embodiments, the compressive strength is 120 MPa or greater (e.g., 120 to 150 MPa).

In a second aspect, the invention features a method of bone repair that includes administering a self-setting, porous calcium phosphate composition having a calcium phosphate, an effervescent agent, and a biocompatible cohesiveness agent admixed with a physiologically acceptable fluid to a subject in need thereof (i.e., the composition as described in the first aspect of the invention). All of the embodiments of the first aspect of the invention apply to the composition utilized in the second aspect of the invention.

As used herein, the term "about" means±10% of the recited value. As used herein and applied to a calcium phosphate, the term "amorphous" means a calcium phosphate having no or only short range crystallographic order, i.e., crystallographic order over less than 100 nm.

By "amorphization" or "amorphicized" is meant a process of mechanical or energetic disruption in the thermodynamically stable form of the ordered, repeating, three-dimensional spatial relationship that exists within a crystal lattice, such as between atoms, molecules, ions, and ligands within a crystalline or semi-crystalline material. The process moves the average material index of crystallinity from its original ordered state to a less ordered state.

As used herein, a "biocompatible" substance is one that does not produce an unacceptable or undesirable physiological response, e.g., an immune response, in the recipient.

As used herein and applied to a composition, the term "cohesiveness" means the ability of the composition, when mixed with a biocompatible fluid, to maintain its shape without loss of mass. A composition is deemed cohesive if greater than 90% of its initial mass and volume are retained within its initial shape dimension following incubation in an aqueous environment for at least 10 minutes.

As used herein, a "cohesiveness agent" means an additive that, when included in a calcium phosphate composition of the invention, improves the ability of the calcium phosphate composition to maintain its cohesiveness. Preferred cohesiveness agents include polymers selected from polysaccharides, nucleic acids, carbohydrates, proteins, polypeptides, poly(α-hydroxy acids), poly(lactones), poly(amino acids), poly(anhydrides), poly(orthoesters), poly(anhydride-co-imides), poly(orthocarbonates), poly(α-hydroxy alkanoates), poly(dioxanones), poly(phosphoesters), poly(L-lactide) (PLLA), poly(D,L-lactide) (PDLLA), polyglycolide (PGA), poly(lactide-co-glycolide (PLGA), poly(L-lactide-co-D, L-lactide), poly(D,L-lactide-co-trimethylene carbonate), polyhydroxybutyrate (PHB), poly(ϵ-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly(ethylene terephthalate) polyamide, and copolymers thereof. Preferred cohesiveness agents also include alginic acid, arabic gum, guar gum, xantham gum, gelatin, chitin, chitosan, chitosan acetate, chitosan lactate, chondroitin sulfate, N,O-carboxymethyl chitosan, a dextran (e.g., α-cyclodextrin, δ-cyclodextrin, γ-cyclodextrin, or sodium dextran sulfate), fibrin glue, glycerol, hyaluronic acid, sodium hyaluronate, a cellulose (e.g., methylcellulose, carboxy methylcellulose, hydroxypropyl methylcellulose, or hydroxyethyl cellulose), a glucosamine, a proteoglycan, a starch (e.g., hydroxyethyl starch or starch soluble), lactic acid, a pluronic, sodium glycerophosphate, collagen, glycogen, a keratin, silk, and mixtures thereof.

By "effervescent agent" is meant an agent capable of producing bubbles of gas in a composition or an agent that emerges from a composition as bubbles of gas; the production or release of the bubbles in the composition being responsible for generating porosity within the composition.

As used herein, "poorly crystalline apatitic (PCA) calcium phosphate" means a synthetic calcium phosphate material having small crystalline domains, on the order of those found in naturally-occurring bone, and characterized by a broad, poorly-defined X-ray diffraction pattern and a Ca/P ratio of less than 1.67. The PCA calcium phosphate is not necessarily restricted to a single calcium phosphate phase, provided it demonstrates the characteristic X-ray diffraction pattern of an apatitic mineral, namely two broad peaks in the region of 20-35° with a peak centered at 26° and a second peak centered at 32°.

BRIEF DESCRIPTION OF THE FIGURE

The invention is described with reference to the following figure, which is presented for the purpose of illustration only and which is not intended to be limiting of the invention.

FIG. 1 illustrates the X-ray diffraction (XRD) pattern of a calcium phosphate powder comprising amorphous calcium phosphate and dicalcium phosphate dihydrate (DCPD) before high energy milling and after high energy milling for 3, 10, 15, and 24 hours in a high energy ball mill.

DETAILED DESCRIPTION OF THE INVENTION

Formable, self-hardening, porous calcium phosphate compositions having a chemical composition comparable to that of natural bone, and which retain cohesiveness when introduced at an implant site in vivo, are provided. These bone implant materials are highly osteoinductive despite their chemical composition. The porosity (number and size of pores) of the calcium phosphate compositions is determined by the rate of release of an effervescent agent that escapes from the mixture during the hardening process. Further, upon hardening, these porous implant materials display significant compressive strength.

The formable, self-hardening, porous calcium phosphate composition includes a calcium phosphate powder, an effervescent agent, and a biocompatible cohesiveness agent (e.g., a binder). Upon combination with a physiologically-acceptable fluid, the calcium phosphate powder produces a formable paste that hardens and reacts to form a poorly-crystalline apatitic calcium phosphate. Preferably the poorly-crystalline apatitic calcium phosphate has a Ca/P ratio of less than 1.67. For example, the poorly-crystalline apatitic calcium phosphate desirably has an overall Ca/P ratio in the range of 1.0-1.67, preferably 1.3-1.65, more preferably 1.4-1.6, and most preferably in the range of 1.45 to 1.67 (i.e., close to that of naturally-occurring bone). Preferably, the poorly-crystalline apatitic calcium phosphate has a Ca/P ratio of about 1.5. This PCA calcium phosphate is remodeled into bone in vivo. The nature of the calcium phosphate powder and/or the presence of the biocompatible cohesiveness agent permit the inclusion of substantial quantities of supplemental materials, e.g., biologically active agents, such as DBM particles, in the bone implant materials without compromising their formability or mechanical strength. Thus, the implant material retains its cohesiveness following implantation at an implant site in vivo and displays significant compressive strength upon hardening. In addition, the inclusion of an effervescent agent promotes the formation of pores in the hardened calcium phosphate implant material that allow the penetration of blood vessels, cells and tissues, and drugs without compromising the mechanical strength of the implant material. Notably, in at least some embodiments, the implant material is highly osteoinductive despite the presence of the inorganic calcium phosphate sources.

One feature of the calcium phosphate compositions is their porosity, which is promoted by the presence of an effervescent agent. Porosity of the calcium phosphate compositions is a desirable characteristic as it facilitates cell migration and infiltration into the calcium phosphate compositions so that the cells can secrete extracellular bone matrix. It also provides access for vascularization. Porosity also provides high surface area for enhanced resorption and release of active substances, as well as increased cell-matrix interaction.

Calcium Phosphates

The calcium phosphate composition of the invention may be prepared using an amorphous calcium phosphate alone or in combination with a second calcium phosphate source. Amorphous calcium phosphate has a broad, diffuse X-ray diffraction pattern, is homogenous when measured on a nanometer scale, and is a gel-like material formed by rapid precipitation from a solution containing calcium and phosphate ion sources. The rapid precipitation creates numerous defects in the calcium phosphate nuclei. Under physiological conditions, amorphous calcium phosphate has a high solubility, high formation rate, and high rate of conversion to PCA calcium phosphate.

Amorphous calcium phosphate has a Ca/P molar ratio in the range of about 1.1 to about 1.9. In at least some embodiments of the instant invention, the amorphous calcium phosphate has a Ca/P molar ratio of less than 1.5. In particular embodiments, the Ca/P molar ratio is between about 1.35 and about 1.49. The Ca/P molar ratio of the amorphous calcium phosphate may be modified by the introduction of additional ions into the calcium and phosphate ion-containing solution. Non-limiting examples of such additional ions include $CO_3^{2-}$, $Mg^{2+}$, $P_2O_7^{4-}$, nitrate, nitrite, or acetate ions. The preparation and characterization of amorphous calcium phosphates are described further in U.S. Pat. Nos. 5,650,176 and 6,214,368, which are incorporated herein by reference.

In at least some embodiments, the amorphous calcium phosphate is present in an amount greater than or equal to about 20 wt % of the powder component. In particular embodiments, the amorphous calcium phosphate is present in an amount greater than or equal to about 30 wt % of the powder component.

In some embodiments, a second calcium phosphate source is included in the calcium phosphate powder. The second calcium phosphate source may be crystalline or amorphous. Appropriate second calcium phosphate sources for use in the instant invention include acidic and neutral calcium phosphates having a stoichiometry such that they produce apatitic calcium phosphates upon reaction with amorphous calcium phosphate. Non-limiting examples of suitable acidic calcium phosphates include calcium metaphosphate, dicalcium phosphate dihydrate, heptacalcium phosphate, tricalcium phosphate, calcium pyrophosphate dihydrate, poorly crystalline hydroxyapatite, calcium pyrophosphate, and octacalcium phosphate. In particular embodiments, the second calcium phosphate source is dicalcium phosphate dihydrate (DCPD).

The amorphous calcium phosphate and the second calcium phosphate source should be selected such that they produce a calcium phosphate powder having a desired overall Ca/P molar ratio. Thus, the amorphous calcium phosphate and the second calcium phosphate source are used in proportions ranging from 1:10 to 10:1, or 1:5 to 5:1, or about 1:1. In at least some embodiments, the desired calcium phosphate product is poorly crystalline apatitic (PCA) calcium phosphate. Because the reaction forming PCA calcium phosphate from the amorphous calcium phosphate and the second calcium phosphate source proceeds substantially to completion, the Ca/P molar ratio of the amorphous calcium phosphate and the second calcium phosphate source should be equivalent to that of the product. PCA calcium phosphate has a Ca/P molar ratio between about 1.1 and about 1.9. Thus, according to at least some embodiments of the instant invention, the amorphous calcium phosphate and the second calcium phosphate source should have a Ca/P molar ratio between about 1.1 and about 1.9. In some embodiments, the Ca/P molar ratio of the amorphous calcium phosphate and the second calcium phosphate source ranges from about 1.1 to about 1.7. Preferably, the amorphous calcium phosphate and the second calcium phosphate source, when combined, form a poorly crystalline apatitic (PCA) calcium phosphate having a Ca/P molar ratio of less than 1.67. Preferred poorly crystalline apatitic calcium phosphate compositions are described in, e.g., U.S. Pat. Nos. 6,027,742, 6,214,368, 6,287,341, 6,331,312, and 6,541,037, all of which are incorporated herein by reference.

A low temperature, high mechanical strength calcium phosphate composition can also be used to prepare the calcium phosphate composition containing an effervescent agent and a cohesiveness agent. Such a low temperature high mechanical strength calcium phosphate composition is described in e.g., U.S. Pat. No. 5,783,217, which is incorporated herein by reference.

Alternatively, an amorphous or nanocrystalline calcium phosphate powder obtained by high energy grinding of a calcium phosphate solid under forces sufficient to mechanically fuse the calcium phosphate solid and to reduce the crystalline domains of the calcium phosphate solid to less than about 100 nm can be used to prepare the porous calcium phosphate composition. High energy grinding can be used to prepare single- and multi-component calcium phosphate powders that have reduced crystallinity, reduced particle size and modified solid state structures. Because the resultant powders have considerably reduced crystallinity, the process is referred to as "amorphization" and the powders are referred to as "amorphicized powders." These changes are used to control the rate of hardening, setting, extent of reaction and/or the hardness of the final product.

In one or more embodiments of this aspect of the present invention, a single calcium phosphate source is subjected to amorphization and combined with an effervescent agent, and a biocompatible cohesiveness agent. It may be desirable to amorphicize (e.g., high energy grind) a single calcium phosphate source in order to increase its reactivity or modify its properties in reactions with other calcium phosphate compounds or other agents. Interaction and reaction of the powders also may occur. The calcium phosphate component of the composition can include the amorphicized calcium phosphate powder alone or it can include the combination of an amorphicized calcium phosphate powder with conventional calcium phosphates, calcium sources and/or phosphate sources to provide the calcium phosphate component. The calcium phosphate composition (consisting of the calcium phosphate powder, the effervescent agent, and the biocompatible cohesiveness agent) is then combined with a hydration medium, such as water, an aqueous solution, e.g., saline or phosphate buffer, or serum to form a hardened, porous calcium phosphate product.

In another embodiment of this aspect of the invention, two or more powders, at least one of which is a calcium phosphate source, are subjected to the high energy grinding process of the invention. Thus, in one or more embodiments, the powder can include two or more calcium phosphates. In one or more embodiments, the calcium phosphate source is combined with a secondary powder such as a phosphate or a calcium source (or other agent as desired) and subjected to high energy grinding to obtain an amorphicized powder. In addition to the effects noted above for a single-component powder, e.g., increased reactivity and reduced crystallinity, high energy grinding of multi-component powders can also promote interaction and reaction between the powders.

The extent of amorphization can be monitored by Fourier Transform infrared spectroscopy and/or X-ray diffraction. Clearly defined peaks in both spectra become broad and poorly defined as crystallinity is reduced, as is described in greater detail below. The amorphicized powders according to one or more embodiments of the present invention have tap densities of greater than 0.7 g/cm$^3$ (compared to tap densities of less than 0.6 g/cm$^3$ for conventional powders). The effectiveness of grinding also affects the porosity of a final hardened calcium phosphate cement prepared from a hydrated powder (paste) containing the amorphicized calcium phosphate powder. The amorphicized powders of the present invention pack more efficiently than their conventional powder counterparts, thereby providing a tightly packed, but porous, calcium phosphate product.

In high energy ball milling, one or more calcium phosphates are placed in a container and ground by randomly moving balls agitated by rotating shafts or arms. Milling machines like those sold under the trademarks Attritor Model 01HD, Fritch Pulverisette 4, ASI Uni-Ball Mill II, and Zoz Simoloyer® may be used. The high energy milling breaks down the calcium phosphate into nanostructural particles on the order of less than about 100 nanometers (nm) having a specific surface area between about 50 m$^2$/g and about 150 m$^2$/g. The nanostructural particles are evenly mixed and form a high-density, homogeneous product powder, which lacks long-range crystalline order. High energy milling processes, including high energy ball milling, and their effects on calcium phosphate sources are further described in copending U.S. patent application Ser. No. 10/222,670, filed on Aug. 16, 2002, and entitled "Synthesis of Calcium Phosphates by Mechano-Chemical Process," which is hereby incorporated by reference in its entirety.

In at least some embodiments, the calcium phosphate is milled for a time less than or equal to about 24 hours. In some embodiments, the calcium phosphate is milled for about 15 hours. In other embodiments, the calcium phosphate is milled for about 3 hours. As the high energy milling time increases, the amorphization of the calcium phosphate increases and its X-ray diffraction pattern becomes broader and more diffuse (see, e.g., FIG. 1).

The calcium phosphate powder will be present in varying amounts depending upon the intended use and desired characteristics of the implant material. In some embodiments, the calcium phosphate powder will be present in an amount between about 20 and about 99 weight percent of the powder component (e.g., at least about 30 weight percent). In other embodiments, the calcium phosphate powder will be present in an amount between about 50 to about 99 weight percent of the powder component (e.g., at least about 85 weight percent).

Effervescent Agents

The porous calcium phosphate composition of the present invention also includes an effervescent agent. The effervescent agent may be a gas which is dissolved in the calcium phosphate composition prior to implantation. The gas may be dissolved in the calcium phosphate composition under pressure, i.e., by subjecting the composite material to a pressurized atmosphere of the gas, but which is inert to the cementing reaction. The gas is then liberated upon exposure to physiological temperatures (i.e., upon injection or implantation), due to the decrease in gas solubility with increased temperature. Under these circumstances, the gas dissolution and subsequent pore formation occurs only during hardening in vivo, and not prior to administration. This is especially attractive since pore formation is not desired to occur at room temperature in the syringe. Suitable gases include, without limitation, carbon dioxide, air, nitrogen, helium, oxygen, and argon.

Alternatively, the effervescent agent may be a solid material which liberates gas upon dissolution. For example, a carbonate, such as sodium bicarbonate, evolves carbon dioxide gas as it converts to an unstable carbonic acid intermediate, which subsequently evolves carbon dioxide and water. In an embodiment, the effervescent agent is sodium bicarbonate, which is present in the calcium phosphate composition in an amount between 0.5 and 40% by weight. A more detailed description of effervescent agents and their use is found in, e.g., U.S. Ser. No. 10/160,607, entitled "Calcium Phosphate Delivery Vehicles for Osteoinductive Proteins," filed on May 31, 2002 and published on Dec. 12, 2002 as U.S. Patent Application Publication No. 20020187104. The effervescent agent may also be a combination of two or more components which, when combined in the presence of a hydrating medium, such as water, pH-buffered saline, and serum, release a gas as a result of a chemical reaction between the two or more components. Preferably, the two or more components are selected and combined in a predetermined molar ratio so as to produce a quantity of gas over a period of time. Release of the gas produced by the two or more components of the effervescent agent at a controlled rate promotes the formation of interconnected pores in the calcium phosphate composition during the hardening process.

Preferably, pore formation in the calcium phosphate compositions of the invention is achieved by adding an effervescent agent and a viscosity modifier (e.g., a biocompatible cohesiveness agent). The effervescent agent is selected to effervesce slowly at biological temperatures, e.g., about 37° C., or, e.g., in a range of between about 30° C. to about 43° C., while the viscosity modifier improves the cohesivity of the cement. The resulting cement is moldable and self-hardening. The hardened cement exhibits a continuous matrix of interconnected porosity.

In other embodiments, the hardened calcium phosphate composition exhibits at least about 5% to 60% porosity. Preferably the calcium phosphate composition has a porosity of about 5%, more preferably about 10, 20, or 30% porosity, and most preferably about 40, 50, or 60% porosity. In a preferred embodiment, the calcium phosphate has at least about 50% porosity. The porosity forms as a result of the action of the controlled release of a gaseous component of the effervescent agent.

In other embodiments, the calcium phosphate is prepared using pre-determined mixtures of two or more components as the effervescent agent, which react when hydrated to produce a gaseous byproduct, the release of which promotes the formation of interconnected pores in the calcium phosphate composition. For example, an effervescent agent can include two components prepared in a predetermined ratio; the first component having the formula $M_xCO_3$, and the second component having the formula $M'_yHCO_3$, in which M and M' are monovalent cations, $x=2$, and $y=1$. Preferred monovalent cations include sodium (Na), potassium (K), lithium (Li), rubidium (Rb), cesium (Cs), silver (Ag), thallium (Tl), and ammonium ($NH_4^+$). Alternatively, M and M' are divalent and monovalent cations, respectively, $x=1$, and $y=1$. Preferred divalent cations include barium (Ba), cadmium (Cd), calcium (Ca), cobalt (Co), copper (Cu), iron (Fe), magnesium (Mg), manganese (Mn), nickel (Ni), strontium (Sr), and zinc (Zn), while preferred monovalent cations include sodium (Na), potassium (K), lithium (Li), rubidium (Rb), cesium (Cs), silver (Ag), thallium (Tl), and ammonium ($NH_4^+$). Porosity of the calcium phosphate composition is controlled by the rate of release of $CO_2$ from this effervescent agent mixture. Prior to solvation, the effervescent agent is stable in solid form. Upon solvation, the rate of release of $CO_2$ from these mixtures depends on: the total solubility product ($K_{sp}$) for the synthetic mixture, and on the molar ratio of $M_xCO_3$ to $M'_yHCO_3$. Preferred molar ratios of carbonate to bicarbonate are those in the range of about 1:1 to about 1:9. More preferably about 1:2, 1:3, 1:4, 1:5, 1:6, 1:7, and 1:8.

In one configuration, a mixture of $Na_2CO_3$ to $NaHCO_3$ (molar ratio 1:9) is added to the calcium phosphate powder and cohesiveness agent. Upon hydration of the mixture with un-buffered solution, a stable paste results which can be formed in-situ, to fill a large range of clinical defects. Controlled pore formation results at body temperature, as the paste material is placed into a defect site. Pore formation continues over nominally 4-5 minutes through the release of $CO_2(g)$, forming a hardened, shape conformed solid, containing interconnected pores exhibiting a median pore size of nominally 10-100 µm, and a compressive strength on the order of at least about 1 MPa, more preferably at least about 10 MPa or more.

In a second configuration, a mixture of $Na_2CO_3$ to $NaHCO_3$ (molar ratio 1:1) is added to the calcium phosphate powder and cohesiveness agent. Upon hydration of the mixture with un-buffered solution, a stable paste results which can be formed in-situ, to fill a large range of clinical defects. Controlled pore formation results at body temperature, as the paste material is placed into a defect site. Pore formation continues over nominally 0-1 minutes through the release of $CO_2(g)$, forming a hardened, shape conformed solid, containing interconnected pores exhibiting a median pore size of nominally 1-10 µm and a compressive strength at least about 1 MPa, more preferably at least about 10 MPa or more.

Biocompatible Cohesiveness Agents

The calcium phosphate composition of the present invention includes a biocompatible cohesiveness agent. Non-limiting examples of suitable biocompatible cohesiveness agents include polymers selected from polysaccharides, nucleic acids, carbohydrates, proteins, polypeptides, poly(α-hydroxy acids), poly(lactones), poly(amino acids), poly(anhydrides), poly(orthoesters), poly(anhydride-co-imides), poly(orthocarbonates), poly(α-hydroxy alkanoates), poly(dioxanones), poly(phosphoesters), poly(L-lactide) (PLLA), poly(D,L-lactide) (PDLLA), polyglycolide (PGA), poly(lactide-co-glycolide) (PLGA), poly(L-lactide-co-D, L-lactide), poly(D,L-lactide-co-trimethylene carbonate), polyhydroxybutyrate (PHB), poly(ε-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly(ethylene terephthalate)polyamide, and copolymers thereof. Preferred cohesiveness agents also include alginic acid, arabic gum, guar gum, xantham gum, gelatin, chitin, chitosan, chitosan acetate, chitosan lactate, chondroitin sulfate, N,O-carboxymethyl chitosan, a dextran (e.g., α-cyclodextrin, β-cyclodextrin, γ-cyclodextrin, or sodium dextran sulfate), fibrin glue, glycerol, hyaluronic acid, sodium hyaluronate, a cellulose (e.g., methylcellulose, carboxy methylcellulose, hydroxypropyl methylcellulose, or hydroxyethyl cellulose), a glucosamine, a proteoglycan, a starch (e.g., hydroxyethyl starch or starch soluble), lactic acid, a pluronic, sodium glycerophosphate, collagen, glycogen, a keratin, silk, and mixtures thereof. In some embodiments, the biocompatible cohesiveness agent is water-soluble. A water-soluble cohesiveness agent dissolves from the implant material shortly after its implantation in vivo, thereby introducing macroporosity into the bone implant material. This macroporosity increases the osteoconductivity of the bone implant material by enhancing the access and, consequently, the remodeling activity of the osteoclasts and osteoblasts at the implant site.

The biocompatible cohesiveness agent may be added to the porous calcium phosphate composition in varying amounts and at a variety of stages during the production of the powder component. The biocompatible cohesiveness agent is present in a range of about 1 to 50 weight percent. In several embodiments of the invention, the biocompatible cohesiveness agent is present in an amount less than or equal to 40 weight percent of the powder component, preferably less than or equal to 30 weight percent, more preferably less than or equal to 20 weight percent, and most preferably less than or equal to 10 weight percent. In a preferred embodiment, the biocompatible cohesiveness agent is present in an amount of about 5 weight percent.

In an embodiment of the invention, the calcium phosphate composition includes DBM. In some instances, the DBM content of the bone implant material is so high that, notwithstanding the formability and cohesiveness provided by the calcium phosphate component of the composition, a cohesiveness agent may be desirable to further augment the mechanical strength of the bone implant material during implantation. In particular embodiments, the biocompatible cohesiveness agent is present in an amount of about 10 weight percent of the powder component. In a preferred embodiment, the calcium phosphate composition includes DBM in an amount of about 40 to 50 weight percent, a calcium phosphate component in an amount of about 35 to 45 weight percent, a cohesiveness agent in an amount of about 5 to 10 weight percent, and an effervescent agent in an amount of about 5 to 10 weight percent, such that the combination of all of the components totals 100 weight percent. The biocompatible cohesiveness agent may be added to the DBM particles as a solution; for example, the cohesiveness agent can coat the DBM particles. The biocompatible cohesiveness agent may be added to the powder component of the composition, including the DBM particles and the calcium phosphate powder. Those of skill in the art will be able to determine the amount of cohesiveness agent and method of inclusion required for a given application.

Biologically Active Agents

The calcium phosphate compositions of the invention can also include a biologically active agent. In general, the biologically active agent should remain active within the paste during manufacture of the porous calcium phosphate, or be capable of being subsequently activated or re-activated following manufacture of the porous calcium phosphate. Alternatively, the biologically active agent can be added at the time of implantation of the porous calcium phosphate composition (whether as a moldable paste or as a hardened cement) into a host or following hardening of the vehicle at 37° C. in an aqueous environment.

Biologically active agents that can be incorporated into the compositions of the invention include, without limitation, organic molecules, inorganic materials, proteins, peptides, nucleic acids (e.g., genes, gene fragments, gene regulatory sequences, and antisense molecules), nucleoproteins, polysaccharides, glycoproteins, and lipoproteins. Classes of biologically active compounds that can be incorporated into the compositions of the invention include, without limitation, anti-cancer agents, antibiotics, analgesics, anti-inflammatory agents, immunosuppressants, enzyme inhibitors, antihistamines, anti-convulsants, hormones, muscle relaxants, anti-spasmodics, ophthalmic agents, prostaglandins, anti-depressants, anti-psychotic substances, trophic factors, osteoinductive proteins, growth factors, and vaccines.

Anti-cancer agents include alkylating agents, platinum agents, antimetabolites, topoisomerase inhibitors, antitumor antibiotics, antimitotic agents, aromatase inhibitors, thymidylate synthase inhibitors, DNA antagonists, farnesyl-transferase inhibitors, pump inhibitors, histone acetyltransferase inhibitors, metalloproteinase inhibitors, ribonucleoside reductase inhibitors, TNF alpha agonists/antagonists, endothelin A receptor antagonists, retinoic acid receptor agonists, immuno-modulators, hormonal and antihormonal agents, photodynamic agents, and tyrosine kinase inhibitors.

Any of the biologically active agents listed in Table 1 can be used.

TABLE 1

| | | |
|---|---|---|
| Alkylating agents | cyclophosphamide | lomustine |
| | busulfan | procarbazine |
| | ifosfamide | altretamine |
| | melphalan | estramustine phosphate |
| | hexamethylmelamine | mechlorethamine |
| | thiotepa | streptozocin |
| | chlorambucil | temozolomide |
| | dacarbazine | semustine |
| | carmustine | |
| Platinum agents | cisplatin | carboplatinum |
| | oxaliplatin | ZD-0473 (AnorMED) |
| | spiroplatinum, | lobaplatin (Aeterna) |
| | carboxyphthalatoplatinum, | satraplatin (Johnson Matthey) |
| | tetraplatin | BBR-3464 (Hoffmann-La Roche) |
| | ormiplatin | SM-11355 (Sumitomo) |
| | iproplatin | AP-5280 (Access) |
| Antimetabolites | azacytidine | tomudex |
| | gemcitabine | trimetrexate |
| | capecitabine | deoxycoformycin |
| | 5-fluorouracil | fludarabine |
| | floxuridine | pentostatin |
| | 2-chlorodeoxyadenosine | raltitrexed |
| | 6-mercaptopurine | hydroxyurea |
| | 6-thioguanine | decitabine (SuperGen) |
| | cytarabin | clofarabine (Bioenvision) |
| | 2-fluorodeoxy cytidine | irofulven (MGI Pharma) |
| | methotrexate | DMDC (Hoffmann-La Roche) |
| | idatrexate | ethynylcytidine (Taiho) |
| Topoisomerase inhibitors | amsacrine | rubitecan (SuperGen) |
| | epirubicin | exatecan mesylate (Daiichi) |
| | etoposide | quinamed (ChemGenex) |
| | teniposide or mitoxantrone | gimatecan (Sigma-Tau) |
| | irinotecan (CPT-11) | diflomotecan (Beaufour-Ipsen) |
| | 7-ethyl-10-hydroxy-camptothecin | TAS-103 (Taiho) |
| | topotecan | elsamitrucin (Spectrum) |
| | dexrazoxanet (TopoTarget) | J-107088 (Merck & Co) |
| | pixantrone (Novuspharma) | BNP-1350 (BioNumerik) |
| | rebeccamycin analogue (Exelixis) | CKD-602 (Chong Kun Dang) |
| | BBR-3576 (Novuspharma) | KW-2170 (Kyowa Hakko) |

TABLE 1-continued

| | | |
|---|---|---|
| Antitumor antibiotics | dactinomycin (actinomycin D)<br>doxorubicin (adriamycin)<br>deoxyrubicin<br>valrubicin<br>daunorubicin (daunomycin)<br>epirubicin<br>therarubicin<br>idarubicin<br>rubidazone<br>plicamycinp<br>porfiromycin<br>cyanomorpholinodoxorubicin<br>mitoxantrone (novantrone) | amonafide<br>azonafide<br>anthrapyrazole<br>oxantrazole<br>losoxantrone<br>bleomycin sulfate (blenoxane)<br>bleomycinic acid<br>bleomycin A<br>bleomycin B<br>mitomycin C<br>MEN-10755 (Menarini)<br>GPX-100 (Gem Pharmaceuticals) |
| Antimitotic agents | paclitaxel<br>docetaxel<br>colchicine<br>vinblastine<br>vincristine<br>vinorelbine<br>vindesine<br>dolastatin 10 (NCI)<br>rhizoxin (Fujisawa)<br>mivobulin (Warner-Lambert)<br>cemadotin (BASF)<br>RPR 109881A (Aventis)<br>TXD 258 (Aventis)<br>epothilone B (Novartis)<br>T 900607 (Tularik)<br>T 138067 (Tularik)<br>cryptophycin 52 (Eli Lilly)<br>vinflunine (Fabre)<br>auristatin PE (Teikoku Hormone)<br>BMS 247550 (BMS)<br>BMS 184476 (BMS)<br>BMS 188797 (BMS)<br>taxoprexin (Protarga) | SB 408075 (GlaxoSmithKline)<br>E7010 (Abbott)<br>PG-TXL (Cell Therapeutics)<br>IDN 5109 (Bayer)<br>A 105972 (Abbott)<br>A 204197 (Abbott)<br>LU 223651 (BASF)<br>D 24851 (ASTAMedica)<br>ER-86526 (Eisai)<br>combretastatin A4 (BMS)<br>isohomohalichondrin-B (PharmaMar)<br>ZD 6126 (AstraZeneca)<br>PEG-paclitaxel (Enzon)<br>AZ10992 (Asahi)<br>IDN-5109 (Indena)<br>AVLB (Prescient NeuroPharma)<br>azaepothilone B (BMS)<br>BNP-7787 (BioNumerik)<br>CA-4 prodrug (OXiGENE)<br>dolastatin-10 (NIH)<br>CA-4 (OXiGENE) |
| Aromatase inhibitors | aminoglutethimide<br>letrozole<br>anastrazole<br>formestane | exemestane<br>atamestane (BioMedicines)<br>YM-511 (Yamanouchi) |
| Thymidylate synthase inhibitors | pemetrexed (Eli Lilly)<br>ZD-9331 (BTG) | nolatrexed (Eximias)<br>CoFactor ™ (BioKeys) |
| DNA antagonists | trabectedin (PharmaMar)<br>glufosfamide (Baxter International)<br>albumin + 32P (Isotope Solutions)<br>thymectacin (NewBiotics)<br>edotreotide (Novartis) | mafosfamide (Baxter International)<br>apaziquone (Spectrum Pharmaceuticals)<br>O6 benzyl guanine (Paligent) |
| Farnesyltransferase inhibitors | arglabin (NuOncology Labs)<br>lonafarnib (Schering-Plough)<br>BAY-43-9006 (Bayer) | tipifarnib (Johnson & Johnson)<br>perillyl alcohol (DOR BioPharma) |
| Pump inhibitors | CBT-1 (CBA Pharma)<br>tariquidar (Xenova)<br>MS-209 (Schering AG) | zosuquidar trihydrochloride (Eli Lilly)<br>biricodar dicitrate (Vertex) |
| Histone acetyltransferase inhibitors | tacedinaline (Pfizer)<br>SAHA (Aton Pharma)<br>MS-275 (Schering AG) | pivaloyloxymethyl butyrate (Titan)<br>depsipeptide (Fujisawa) |
| Metalloproteinase inhibitors | Neovastat (Aeterna Laboratories)<br>marimastat (British Biotech) | CMT-3 (CollaGenex)<br>BMS-275291 (Celltech) |
| Ribonucleoside reductase inhibitors | gallium maltolate (Titan)<br>triapine (Vion) | tezacitabine (Aventis)<br>didox (Molecules for Health) |
| TNF alpha agonists/antagonists | virulizin (Lorus Therapeutics)<br>CDC-394 (Celgene) | revimid (Celgene) |
| Endothelin A receptor antagonist | atrasentan (Abbott)<br>ZD-4054 (AstraZeneca) | YM-598 (Yamanouchi) |
| Retinoic acid receptor agonists | fenretinide (Johnson & Johnson)<br>LGD-1550 (Ligand) | alitretinoin (Ligand) |
| Immuno-modulators | interferon<br>oncophage (Antigenics)<br>GMK (Progenics)<br>adenocarcinoma vaccine (Biomira)<br>CTP-37 (AVI BioPharma)<br>IRX-2 (Immuno-Rx)<br>PEP-005 (Peplin Biotech)<br>synchrovax vaccines (CTL Immuno)<br>melanoma vaccine (CTL Immuno)<br>p21 RAS vaccine (GemVax) | dexosome therapy (Anosys)<br>pentrix (Australian Cancer Technology)<br>ISF-154 (Tragen)<br>cancer vaccine (Intercell)<br>norelin (Biostar)<br>BLP-25 (Biomira)<br>MGV (Progenics)<br>β-alethine (Dovetail)<br>CLL therapy (Vasogen) |

TABLE 1-continued

| | | |
|---|---|---|
| Hormonal and antihormonal agents | estrogens<br>conjugated estrogens<br>ethinyl estradiol<br>chlortrianisen<br>idenestrol<br>hydroxyprogesterone caproate<br>medroxyprogesterone<br>testosterone<br>testosterone propionate; fluoxymesterone<br>methyltestosterone<br>diethylstilbestrol<br>megestrol<br>tamoxifen<br>toremofine<br>dexamethasone | prednisone<br>methylprednisolone<br>prednisolone<br>aminoglutethimide<br>leuprolide<br>goserelin<br>leuporelin<br>bicalutamide<br>flutamide<br>octreotide<br>nilutamide<br>mitotane<br>P-04 (Novogen)<br>2-methoxyestradiol (EntreMed)<br>arzoxifene (Eli Lilly) |
| Photodynamic agents | talaporfin (Light Sciences)<br>Theralux (Theratechnologies)<br>motexafin gadolinium (Pharmacyclics) | Pd-bacteriopheophorbide (Yeda)<br>lutetium texaphyrin (Pharmacyclics)<br>hypericin |
| Tyrosine Kinase Inhibitors | imatinib (Novartis)<br>leflunomide (Sugen/Pharmacia)<br>ZD1839 (AstraZeneca)<br>erlotinib (Oncogene Science)<br>canertinib (Pfizer)<br>squalamine (Genaera)<br>SU5416 (Pharmacia)<br>SU6668 (Pharmacia)<br>ZD4190 (AstraZeneca)<br>ZD6474 (AstraZeneca)<br>vatalanib (Novartis)<br>PKI166 (Novartis)<br>GW2016 (GlaxoSmithKline)<br>EKB-509 (Wyeth)<br>EKB-569 (Wyeth) | kahalide F (PharmaMar)<br>CEP-701 (Cephalon)<br>CEP-751 (Cephalon)<br>MLN518 (Millenium)<br>PKC412 (Novartis)<br>phenoxodiol ( )<br>trastuzumab (Genentech)<br>C225 (ImClone)<br>rhu-Mab (Genentech)<br>MDX-H210 (Medarex)<br>2C4 (Genentech)<br>MDX-447 (Medarex)<br>ABX-EGF (Abgenix)<br>IMC-1C11 (ImClone) |

Antibiotics include aminoglycosides (e.g., gentamicin, tobramycin, netilmicin, streptomycin, amikacin, neomycin), bacitracin, corbapenems (e.g., imipenem/cislastatin), cephalosporins, colistin, methenamine, monobactams (e.g., aztreonam), penicillins (e.g., penicillin G, penicillin V, methicillin, natcillin, oxacillin, cloxacillin, dicloxacillin, ampicillin, amoxicillin, carbenicillin, ticarcillin, piperacillin, mezlocillin, azlocillin), polymyxin B, quinolones, and vancomycin; and bacteriostatic agents such as chloramphenicol, clindanyan, macrolides (e.g., erythromycin, azithromycin, clarithromycin), lincomyan, nitrofurantoin, sulfonamides, tetracyclines (e.g., tetracycline, doxycycline, minocycline, demeclocyline), and trimethoprim. Also included are metronidazole, fluoroquinolones, and ritampin.

Enzyme inhibitors are substances which inhibit an enzymatic reaction. Examples of enzyme inhibitors include edrophonium chloride, N-methylphysostigmine, neostigmine bromide, physostigmine sulfate, tacrine, tacrine,1-hydroxy maleate, iodotubercidin, p-bromotetramisole, 10-(alpha-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylamine, $N^6$-monomethyl-L-arginine acetate, carbidopa, 3-hydroxybenzylhydrazine, hydralazine, clorgyline, deprenyl, hydroxylamine, iproniazid phosphate, 6-MeO-tetrahydro-9H-pyrido-indole, nialamide, pargyline, quinacrine, semicarbazide, tranylcypromine, N,N-diethylaminoethyl-2,2-diphenylvalerate hydrochloride, 3-isobutyl-1-methylxanthne, papaverine, indomethacind, 2-cyclooctyl-2-hydroxyethylamine hydrochloride, 2,3-dichloro-a-methylbenzylamine (DCMB), 8,9-dichloro-2,3,4, 5-tetrahydro-1H-2-benzazepine hydrochloride, p-aminoglutethimide, p-aminoglutethimide tartrate, 3-iodotyrosine, alpha-methyltyrosine, acetazolamide, dichlorphenamide, 6-hydroxy-2-benzothiazolesulfonamide, and allopurinol.

Antihistamines include pyrilamine, chlorpheniramine, and tetrahydrazoline, among others.

Anti-inflammatory agents include corticosteroids, nonsteroidal anti-inflammatory drugs (e.g., aspirin, phenylbutazone, indomethacin, sulindac, tolmetin, ibuprofen, piroxicam, and fenamates), acetaminophen, phenacetin, gold salts, chloroquine, D-Penicillamine, methotrexate colchicine, allopurinol, probenecid, and sulfinpyrazone.

Muscle relaxants include mephenesin, methocarbomal, cyclobenzaprine hydrochloride, trihexylphenidyl hydrochloride, levodopa/carbidopa, and biperiden.

Anti-spasmodics include atropine, scopolamine, oxyphenonium, and papaverine.

Analgesics include aspirin, phenylbutazone, idomethacin, sulindac, tolmetic, ibuprofen, piroxicam, fenamates, acetaminophen, phenacetin, morphine sulfate, codeine sulfate, meperidine, nalorphine, opioids (e.g., codeine sulfate, fentanyl citrate, hydrocodone bitartrate, loperamide, morphine sulfate, noscapine, norcodeine, normorphine, thebaine, nor-binaltorphimine, buprenorphine, chlornaltrexamine, funaltrexamione, nalbuphine, nalorphine, naloxone, naloxonazine, naltrexone, and naltrindole), procaine, lidocain, tetracaine and dibucaine.

Ophthalmic agents include sodium fluorescein, rose bengal, methacholine, adrenaline, cocaine, atropine, alpha-chymotrypsin, hyaluronidase, betaxalol, pilocarpine, timolol, timolol salts, and combinations thereof.

Prostaglandins are art recognized and are a class of naturally occurring chemically related, long-chain hydroxy fatty acids that have a variety of biological effects.

Anti-depressants are substances capable of preventing or relieving depression. Examples of anti-depressants include imipramine, amitriptyline, nortriptyline, protriptyline, desipramine, amoxapine, doxepin, maprotiline, tranylcypromine, phenelzine, and isocarboxazide.

Trophic factors are factors whose continued presence improves the viability or longevity of a cell. Trophic factors include, without limitation, platelet-derived growth factor (PDGP), neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, glial derived growth neurotrophic factor, ciliary neurotrophic factor, nerve growth factor, bone growth/cartilage-inducing factor (alpha and beta), bone morphogenetic proteins, interleukins (e.g., interleukin inhibitors or interleukin receptors, including interleukin 1 through interleukin 10), interferons (e.g., interferon alpha, beta and gamma), hematopoietic factors, including erythropoietin, granulocyte colony stimulating factor, macrophage colony stimulating factor and granulocyte-macrophage colony stimulating factor; tumor necrosis factors, transforming growth factors (beta), including beta-1, beta-2, beta-3, inhibin, and activin; and bone morphogenetic proteins such as OP-1, BMP-2 and BMP-7.

Hormones include estrogens (e.g., estradiol, estrone, estriol, diethylstibestrol, quinestrol, chlorotrianisene, ethinyl estradiol, mestranol), anti-estrogens (e.g., clomiphene, tamoxifen), progestins (e.g., medroxyprogesterone, norethindrone, hydroxyprogesterone, norgestrel), antiprogestin (mifepristone), androgens (e.g, testosterone cypionate, fluoxymesterone, danazol, testolactone), anti-androgens (e.g., cyproterone acetate, flutamide), thyroid hormones (e.g., tri-iodothyronne, thyroxine, propylthiouracil, methimazole, and iodixode), and pituitary hormones (e.g., corticotropin, sumutotropin, oxytocin, and vasopressin). Hormones are commonly employed in hormone replacement therapy and/or for purposes of birth control. Steroid hormones, such as prednisone, are also used as immunosuppressants and anti-inflammatories.

Osteogenic Proteins

The biologically active agent is desirably selected from the family of proteins known as the transforming growth factors-beta (TGF-β) superfamily of proteins, which includes the activins, inhibins, and bone morphogenetic proteins (BMPs). Most preferably, the active agent includes at least one protein selected from the subclass of proteins known generally as BMPs, which have been disclosed to have osteogenic activity, and other growth and differentiation type activities. These BMPs include BMP proteins BMP-2, BMP-3, BMP-3b, BMP-4, BMP-5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO 91/18098; and BMP-9, disclosed in PCT publication WO 93/00432, BMP-10, disclosed in PCT application WO 94/26893; BMP-11, disclosed in PCT application WO 94/26892, or BMP-12 or BMP-13, disclosed in PCT application WO 95/16035; BMP-14; BMP-15, disclosed in U.S. Pat. No. 5,635,372; or BMP-16, disclosed in U.S. Pat. No. 5,965,403. Other BMPs include BMP-17 and BMP-18.

Other TGF-β proteins which may be useful as the active agent in the calcium phosphate compositions of the invention include Vgr-2, Jones et al., Mol. Endocrinol. 6:1961 (1992), and any of the growth and differentiation factors (GDFs), including those described in PCT applications WO 94/15965; WO 94/15949; WO 95/01801; WO 95/01802; WO 94/21681; WO 94/15966; WO 95/10539; WO 96/01845; WO 96/02559 and others. Also useful in the invention may be BIP, disclosed in WO 94/01557; HP00269, disclosed in JP Publication number: 7-250688; and MP52, disclosed in PCT application WO 93/16099. The disclosures of all of the above applications are incorporated herein by reference. A subset of BMPs which are presently preferred for use in the invention include BMP-2, BMP-4, BMP-5, BMP-6, BMP-7, BMP-10, BMP-12, BMP-13, BMP-14, and MP52. The active agent is most preferably BMP-2, the sequence of which is disclosed in U.S. Pat. No. 5,013,649, the disclosure of which is incorporated herein by reference. Other osteogenic agents known in the art can also be used, such as teriparatide (Forteo™), Chrysalin®, prostaglandin E2, or LIM protein, among others.

The biologically active agent may be recombinantly produced, or purified from a protein composition. The active agent, if a TGF-β, such as a BMP, or other dimeric protein, may be homodimeric, or may be heterodimeric with other BMPs (e.g., a heterodimer composed of one monomer each of BMP-2 and BMP-6) or with other members of the TGF-β superfamily, such as activins, inhibins and TGF-β1(e.g., a heterodimer composed of one monomer each of a BMP and a related member of the TGF-β superfamily). Examples of such heterodimeric proteins are described for example in Published PCT Patent Application WO 93/09229, the specification of which is hereby incorporated herein by reference.

The biologically active agent may further include additional agents such as the Hedgehog, Frazzled, Chordin, Noggin, Cerberus and Follistatin proteins. These families of proteins are generally described in Sasai et al., Cell 79:779-790 (1994) (Chordin); PCT Patent Publication WO 94/05800 (Noggin); and Fukui et al., Devel. Biol. 159:131 (1993) (Follistatin). Hedgehog proteins are described in WO 96/16668; WO 96/17924; and WO 95/18856. The Frazzled family of proteins is a recently discovered family of proteins with high homology to the extracellular binding domain of the receptor protein family known as Frizzled. The Frizzled family of genes and proteins is described in Wang et al., J. Biol. Chem. 271:4468-4476 (1996). The active agent may also include other soluble receptors, such as the truncated soluble receptors disclosed in PCT patent publication WO 95/07982. From the teaching of WO 95/07982, one skilled in the art will recognize that truncated soluble receptors can be prepared for numerous other receptor proteins. The above publications are hereby incorporated by reference herein. The amount of osteogenic protein effective to stimulate increased osteogenic activity of present or infiltrating progenitor or other cells will depend upon the size and nature of the defect being treated, as well as the carrier being employed.

Generally, the biologically active agent is included in the calcium phosphate composition in an amount sufficient to treat or ameliorate a bone defect or injury, when the calcium phosphate composition is being used in connection with bone regeneration, or in an amount sufficient to treat or prevent a disease or disorder, when the calcium phosphate composition is being used as a depot vehicle for delivery of the biologically active agent. By "an amount sufficient" is meant the amount of a biologically active agent required in the calcium phosphate composition to promote a clinically relevant effect. A sufficient amount of a biologically active compound used to practice the present invention for therapeutic purposes varies depending upon the manner of administration, the age, body weight, and general health of the patient. Ultimately, the prescribers will decide the appropriate amount and dosage regimen. The appropriate amounts for any monotherapy or combination therapy described herein can be determined from animal models, in vitro assays, and/or clinical studies.

By way of example, the amount of a biologically active agent included in the calcium phosphate composition can be in the range of from about 0.1 ng to about 1.0 g; preferably about 1.0 µg to about 100.0 mg; most preferably about 10.0 µg to about 1.0 mg.

Biologically active agents can be introduced into the calcium phosphate compositions of the invention during or after its formation. Agents may conveniently be mixed into the compositions prior to setting. Alternatively, the vehicle may be shaped and hardened and then exposed to the therapeutic agent in solution. This particular approach is particularly well suited for proteins, which are known to have an affinity for apatitic materials. A buffer solution containing the biologically active agent may be employed, instead of water, as the aqueous solution in which the self-hardening paste is, for example, irrigated prior to implantation. Buffers may be used in any pH range, but most often will be used in the range of 5.0 to 8.0 in preferred embodiments the pH will be compatible with prolonged stability and efficacy of the desired therapeutic agent and, in most preferred embodiments, will be in the range of 5.5 to 7.4. Suitable buffers include, but are not limited to, carbonates, phosphates (e.g., phosphate buffered saline), and organic buffers such as Tris, HEPES, and MOPS. Most often, the buffer will be selected for it's biocompatibility with the host tissues and its compatibility with the therapeutic agent. For most applications of nucleic acids, peptides or antibiotics a simple phosphate buffered saline will suffice.

Demineralized Bone Matrix

In a preferred embodiment, the biologically active agent is DBM. DBM is an organic, osteoinductive material most commonly obtained from long bone chips demineralized by acid treatment. The acid treatment dissolves inorganic mineral components and acid-soluble proteins in the bone, leaving behind a collagen matrix as well as acid-insoluble proteins and growth factors (see, e.g., Glowacki et al. (1985) *Clin. Plast. Surg.* 12(2):233-241; Covey et al. (1989) *Orthop. Rev.* 17(8):857-863). Among the residual acid-insoluble proteins and growth factors are osteoinductive factors, such as bone morphogenic proteins (BMPs) and transforming growth factors (TGFs). Thus, DBM is osteoinductive, fully resorbable, and, when used in combination with the calcium phosphate powders described herein, yields bone implant materials that are highly biocompatible because they closely mimic the chemical composition of natural bone. Advantageously, DBM costs less than many other available organic bone composition additives, such as isolated BMPs.

The DBM employed in the calcium phosphate compositions of the invention is preferably derived from autogenic or allogenic sources. As discussed above, DBM may be obtained by acid treatment of long bone chips, a process well known to those of ordinary skill in the art. Alternatively, commercially-available DBM may be used (e.g., DBM available from Allosource, American Red Cross, Musculoskeletal Transplant Foundation, Regeneration Technologies, Inc., and Osteotech, Inc.).

In at least some embodiments, the DBM in the bone implant materials is present in an amount between about 10 and about 70 weight percent of the powder component. In particular embodiments, the DBM is present in an amount equal to about 60 weight percent of the powder component. In other embodiments, the DBM is present in an amount between about 1 and about 50 weight percent of the powder component. In still other embodiments, the DBM is present in an amount less than or equal to about 20 weight percent of the powder component. Preferably, the DBM is present in an amount less than or equal to about 15 weight percent of the powder component.

The amount of DBM in a given composition will vary depending upon the amount of the biocompatible cohesiveness agent, as well as the intended use and desired characteristics of the calcium phosphate composition. In particular embodiments, the cohesiveness agent and the DBM are present in the calcium phosphate composition in a ratio of about 1:1 (e.g., in an amount in the range of about 0.5 and about 20 weight percent of the powder component), preferably about 1:5, more preferably about 1:10, and most preferably about 1:20. In preferred embodiments, the cohesiveness agent is present in an amount of about 5 weight percent or less.

Those of skill in the art will be able to determine the amount of DBM, calcium phosphate, effervescent agent, and cohesiveness agent required for particular applications. For example, a preferred calcium phosphate powder composition includes about 15 weight percent DBM and about 85 weight percent calcium phosphate powder having between about 1 to about 10 weight percent cohesiveness agent and effervescent agent. Another preferred calcium phosphate powder composition includes about 45 weight percent DBM, about 45 weight percent calcium phosphate powder, and about 10 weight percent biocompatible cohesiveness agent and effervescent agent.

The DBM particles may be of various sizes and physical forms. As with the amount of DBM, the size and form of the DBM particles will vary depending upon the intended use of the bone implant material. In some embodiments, the DBM particles have a longest dimension measuring between about 35 μm and about 850 μm and may further have an aspect ratio of less than about 5. In other embodiments, the DBM particles are fibrous in nature. In some embodiments, these DBM fibers have a length between about 50 μm and about 3mm. In other embodiments, these DBM fibers have a length between about 250 μm and about 2 mm. In some embodiments, the aspect ratio of these DBM fibers is greater than 4. In other embodiments, the aspect ratio of these DBM fibers is greater than 10. The DBM fibers may be needle-like, having an average width to average thickness ratio of less than 5. Methods of producing DBM particles of varying sizes will be well-known to those of skill in the art and are disclosed, for example, in co-pending U.S. patent application Ser. No. 10/298,112, filed on Nov. 15, 2002, and entitled "Cohesive Demineralized Bone Compositions," which is incorporated herein by reference. Of note, the needle-like, fibrous DBM obtained from long bone chips or shavings, as opposed to DBM obtained from ground bone, provide increased cohesiveness when incorporated into the calcium phosphate compositions of the present invention.

The incorporation of DBM into calcium phosphate-based bone implant materials has heretofore been limited, due to the tendency of DBM to reduce the mechanical strength of the implant materials into which it is incorporated. Thus, implant materials containing quantities of DBM necessary to maximize its osteoinductive capabilities are difficult to manipulate, lack formability, and lose their cohesiveness and shape following implantation in vivo. The hardened calcium phosphate product is also much weaker. Moreover, the effective use of DBM in bone implant materials containing inorganic, osteoconductive components, such as calcium phosphates, has been heretofore unsuccessful because the inorganic components inhibit the osteoinductivity of the DBM.

The calcium phosphate compositions of the present invention overcome these known deficiencies by including a biocompatible cohesiveness agent, which provides excellent formability and cohesiveness properties to the calcium phosphate composition in the presence of biologically active agents, such as DBM. The calcium phosphate compositions of the present invention also include an effervescent agent, which promotes the formation of interconnected pores without reducing the mechanical strength of the hardened calcium phosphate composition. The pores facilitate migration and infiltration of cells, which can secrete extracellular bone matrix, into the calcium phosphate composition. The pores also provide access for vascularization and a high surface area for enhanced resorption and release of active substances and increased cell-matrix interaction.

Standard protocols and regimens for delivery of the above-listed agents are known in the art. Biologically active agents are introduced into the calcium phosphate vehicle in amounts that allow delivery of an appropriate dosage of the agent to the implant site. In most cases, dosages are determined using guidelines known to practitioners and applicable to the particular agent in question. The exemplary amount of biologically active agent to be included in the calcium phosphate paste of the invention or added to the hardened delivery vehicle is likely to depend on such variables as the type and extent of the condition, the overall health status of the particular patient, the formulation of the active agent, and the bioresorbability of the delivery vehicle used. Standard clinical trials may be used to optimize the dose and dosing frequency for any particular biologically active agent.

In at least some embodiments, a suitable amount of a physiologically-acceptable fluid is added to the powder component to produce a self-hardening paste or putty. Non-limiting examples of suitable physiologically-acceptable fluids include water, saline, phosphate buffers, and biological fluids. Biological fluids include any treated or untreated fluid (including a suspension) associated with living organisms, particularly blood, including whole blood, warm or cold blood, and stored or fresh blood; treated blood, such as blood diluted with at least one physiological solution, including but not limited to saline, nutrient, and/or anticoagulant solutions; blood components, such as platelet concentrate (PC), apheresed platelets, platelet-rich plasma (PRP), platelet-poor plasma (PPP), platelet-free plasma, plasma, serum, fresh frozen plasma (FFP), components obtained from plasma, packed red cells (PRC), buffy coat (BC); blood products derived from blood or a blood component or derived from bone marrow; red cells separated from plasma and resuspended in physiological fluid; and platelets separated from plasma and resuspended in physiological fluid. Biological fluids also include, e.g., milk, urine, saliva, seminal or vaginal fluid, synovial fluid, lymph fluid, amniotic fluid, the fluid within the yolk sac, the chorion, or the allantois of an egg, sweat, and tears.

These paste compositions have improved flow characteristics compared to most previously-known bone implant materials, which are attributable to the inclusion of amorphous calcium phosphate and the nature of the calcium phosphate powder. Varying amounts of fluid may be added to the powder to produce a paste having the desired characteristics. For example, in at least some embodiments, 0.5-2.0 cc of fluid per gram of powder is used to prepare a paste that is formable, i.e., capable of being molded and retaining its shape. In at least some embodiments, the paste is injectable, i.e., capable of passing through a 16- to 18-gauge syringe.

Following the addition of the physiologically-acceptable fluid and an appropriate amount of an effervescent agent, the paste is delivered to the implant site. The paste may be injected into the implant site or formed into the desired shape and packed into the implant site. The paste may be formed into the desired shape and allowed to harden before being placed into the implant site. Pre-formed devices may be hand shaped, molded, or machined. Those of skill in the art will recognize implantation procedures appropriate for a given application.

The calcium phosphate compositions of the invention exhibit a Ca/P molar ratio similar to that of naturally-occurring bone. The Ca/P molar ratio is between about 1.1 and about 1.9. In some embodiments, the Ca/P molar ratio is between 1.2 and 1.67. Preferably the Ca/P molar ratio is less than 1.67, and may be less than about 1.5.

The conversion of the paste to a hardened calcium phosphate occurs at ambient or body temperatures. The hardening process is not adversely affected by the addition of a biologically active agent, such as DBM, a biocompatible cohesiveness agent, or an effervescent agent. The "self-hardening" or "self-setting" of the calcium phosphate compositions occurs slowly at ambient temperatures, i.e., between about 20° C. and 25° C., and is accelerated significantly at body temperatures, i.e., between about 32° C. and about 37° C. Thus, for example, the paste hardens at ambient temperatures after a time between about 20 minutes to about 60 minutes, while at body temperature, the paste hardens after a time between about 3 minutes and about 15 minutes. The formation and setting characteristics of calcium phosphates are further described in, e.g., U.S. Pat. Nos. 6,214,368, 6,027,742, and 5,650,176, which are incorporated herein by reference.

The hardened calcium phosphate composition of the invention displays significant compressive strength, despite the inclusion of pores caused by the effervescent agent. Compressive strength is a particularly desirable attribute for certain types of bone implants, such as spinal implants. According to some embodiments, the calcium phosphate bone implant materials have a compressive strength greater than about 1 MPa. In particular embodiments, the compressive strength is between 1 MPa and 20 MPa, and may be as high as 30, 40, 50, 60, 70, 80, 90, or 100 MPa. Compressive strengths of over 100 MPa, e.g., 120-150 MPa, can also be achieved. In other particular embodiments, the compressive strength is at least between 2 MPa and 10 MPa. Compositions having about 5% to about 60% porosity resulting from the action of the effervescent agent retain a compressive strength of at least about 1 MPa, and can even exhibit a compressive strength as great as 100 MPa.

Once the paste has converted to a hardened calcium phosphate, the calcium phosphate is remodeled into bone in vivo. As described above, the calcium phosphate has a chemical composition and crystalline structure similar to that of natural bone and is resorbable in biological systems. Remodeling involves slow degradation of the calcium phosphate and use by the body of the resulting calcium and phosphate materials to generate new bone. Remodeling of the bone implant materials prepared according to one or more embodiments of the invention is a long-term process, usually occurring on a time scale of months to years. Bone implant materials of higher densities require longer remodeling periods because the high density and lower porosity of the implants slows penetration by cells and biological substances, causing remodeling to occur as a long-term inward diffusion process. The calcium phosphate implant of the present invention is characterized by increased remodeling due to its increased porosity.

The invention is illustrated by the following examples, which are not intended to be limiting of the invention.

EXAMPLES

Example 1

Preparation of Demineralized Bone Matrix Fibers

This Example describes the preparation of DBM particles that are fibrous in nature.

Long bones were cleaned to remove all connective tissue. The end plates were removed to isolate the cortical bone component of the long bone, and the marrow was removed.

The hollow long bones were washed in alcohol to further clean and remove fat. The bones were then turned on a lathe. Shavings were made by pressing a straight-edged silicon carbide cutting tool into the surface of the bone. The cutting tool advances along the length of the bone to provide a length of bone shaving. The rate of rotation of the bone in concert with the rate of motion of the cutting tool can be controlled by those familiar with the process so as to control the rate of material removal. Shavings of thickness varying between 50 µm and 250 µm, widths between 2 mm and 10 mm and random length were obtained by this process. These shaving were then washed in ether to remove the remaining fats. Demineralization was performed by stirring the shavings in 0.5 molar hydrochloric acid (HCl) for 1 hour. After demineralization, the fibers were rinsed in deionized water until the excess acid was removed. The fibers were then dried by rinsing in alcohol and ether and allowing the ether to evaporate. The average fiber length was distributed randomly between about 250 µm and 2 mm, and average fiber thickness was between about 50 µm and 250 µm.

Example 2

Preparation of Amorphous Calcium Phosphate

This Example describes the preparation of an amorphous calcium phosphate powder.

A solution of 1000 g of disodium hydrogen phosphate heptahydrate ($Na_2HPO_4.7H_2O$) in 14.4 mL distilled water was prepared and stirred. To this solution, 555 g sodium hydroxide (NaOH), 333 g sodium bicarbonate ($NaHCO_3$), and 2.2 g sodium pyrophosphate decahydrate ($Na_4P_2O_7.10H_2O$) were added sequentially to form solution 1.

A solution of 208 g of calcium nitrate tetrahydrate ($Ca(NO_3)_2.4H_2O$) in 5.6 L of distilled water was prepared and stirred. 11 g of magnesium chloride hexahydrate ($MgCl_2.6H_2O$) was added to this solution to form solution 2.

Solution 2 was quickly poured into solution 1 at room temperature and stirred for 1 minute. The amorphous calcium phosphate precipitated immediately and completely. The pH of the suspension was 13±0.5, which was maintained to avoid conversion of the precipitate to an apatite or other more crystalline calcium phosphate.

The precipitate was then immediately separated from its mother solution using a basket centrifugal filtration process and washed using about 100 L of distilled water. Completion of the washing process was confirmed by the last wash ionic conductivity less than 300 µs. This process yields a gel cake of about 500 g of amorphous calcium phosphate.

The wet cake of amorphous calcium phosphate was immediately lyophilized so as to preserve the amorphous structure during drying. About 80% of the water was removed. About 100 g of the lyophilized powder was calcinated at 450° C. for 1 hour.

The amorphous calcium phosphate product had a Ca/P ratio of less than 1.5, and typically between 1.35 and 1.49.

Example 3

Preparation of Dicalcium Phosphate Dihydrate (DCPD)

This Example describes the preparation of dicalcium phosphate dihydrate powder. 20 g diammonium hydrogen phosphate (($NH_4)_2.HPO_4$) was dissolved in 1 L distilled water to prepare solution 3, having a concentration of 0.15 M available phosphate ($PO_4^{-3}$). It was verified that the pH of solution 3 was between 7.0 and 9.0.

35.5 g calcium nitrate tetrahydrate ($Ca(NO_3)_2.4H_2O$) was dissolved in 0.5 L distilled water to prepare solution 4, having a concentration of 0.3M available calcium ($Ca^{+2}$). It was verified that the pH of solution 4 was between 5.0 and 8.0

Solution 4 was poured into solution 3, followed by stifling for about 2 minutes. It was verified that the pH of the resulting suspension was between 5.2 and 6.2. The suspension was filtered by vacuum filtration to form a uniform cake. The cake was washed three times with 750 mL distilled water (2.25 L total). When washing was complete, the cake was separated from the filter paper and dried in a laminar flow hood for 24 hours. The dried powder was milled through a 120 µm nominal pore size screen.

Example 4

Preparation of Calcium Phosphate Powder

This Example describes the preparation of a calcium phosphate powder comprising an amorphous calcium phosphate and a second calcium phosphate source.

Amorphous calcium phosphate, prepared as described in Example 2, and crystalline DCPD, prepared as described in Example 3, were combined in a 1:1 ratio by weight (e.g. 25 g each). The mixed powder was high energy milled in a Ball Mill at 100 RPM for about 3 hours. The average crystalline domain size of the resulting powder was less than about 100 nm.

Example 5

Preparation of DBM/Calcium Phosphate Powder

This Example describes the preparation of a powder comprising DBM particles and a calcium phosphate powder.

0.4 g fibrous DBM particles, prepared as described in Example 1, and 0.6 g calcium phosphate powder, prepared as described in Example 4, were combined using a Turbula mixer.

Example 6

Preparation of DBM/Calcium Phosphate/Cohesiveness Agent Powder

This Example describes the preparation of a powder comprising DBM particles, a calcium phosphate powder, and a biocompatible cohesiveness agent.

0.5 g DBM particles, prepared as described in Example 1, 0.45 g calcium phosphate powder, prepared as described in Example 4, and 0.05 g carboxymethylcellulose were combined in a mixing jar. The resulting powder contained about 50 wt % DBM particles, about 45 wt % calcium phosphate powder, and about 5 wt % carboxymethylcellulose.

Example 7

Preparation of DBM/Calcium Phosphate/Effervescent agent/Cohesiveness Agent Powder This Example describes the preparation of a powder comprising demineralized bone particles, a calcium phosphate powder, an effervescent agent and a biocompatible cohesiveness agent.

0.50 g of human demineralized bone powder obtained from a tissue bank, 0.40 g calcium phosphate powder, prepared as described in Example 4, 0.05 g of sodium bicarbonate, and 0.05 g carboxymethylcellulose were combined in a silicone mixing bulb.

Example 8

Preparation of Calcium Phosphate/Effervescent agent/Cohesiveness Agent Powder This Example describes the preparation of a powder comprising a calcium phosphate powder, an effervescent agent and a biocompatible cohesiveness agent.

0.85 g calcium phosphate powder, prepared as described in Example 4, 0.1 g of Effersoda (1:9 molar ratio of carbonate/bicarbonate), and 0.05 g carboxymethylcellulose were combined in a silicone mixing bulb.

Example 9

Preparation of Formable, Self-Hardening Paste

This Example describes the preparation of a formable, self-hardening paste from the powders described above.

1.0 g samples of each of the powders described in examples 4-8 were each mixed with sufficient saline (0.9% USP), between 0.2 and 2.0 cc, to form a moldable paste.

The resultant pastes were formable, extrudable through a syringe, cohesive in moist environments, and hardened in less than 20 minutes at 37° C.

0.10 cc of the paste was extruded through a 1 cc Becton Dickinson slip tip syringe, having a cut-off tip, to form a 0.1 cc paste cylinder.

Example 10

Cohesiveness of the Formable, Self-Hardening Paste

This Example describes the evaluation of the cohesiveness of a formable, self-hardening paste prepared according to the instant invention.

A 1.0 g sample of the pastes prepared as described in Example 9 were formed into a ball about 1.0 cm in diameter, and the ball was dropped into a beaker of water. The ball retained its initial shape, without significant observable distortion, swelling, or mass loss, for at least 10 minutes. The sample was removed from the water, and the water was filtered to determine the extent of mass lost from the sample upon immersion. No measurable amount of mass loss was observed.

Example 11

Compressive Strength of CaP/Effervescent agent/DBM Composition

This Example describes the evaluation of the wet compressive strength of a formable, self-hardening paste prepared according to the instant invention.

Five grams of powder described in Example 8 were hydrated with 0.35 cc physiological saline per gram powder to form a paste.

The paste can be evenly loaded into 5 cylindrical stainless steel molds measuring 6 mm in diameter and 12 mm in height. The molds are then immersed into a 37° C. physiological saline bath for 2 hours.

The five hardened samples can be removed from the molds and tested for compressive strength using a universal testing machine (Instron, Canton, Mass.) at a crosshead speed of 5 mm/minutes. An evaluation of the calcium phosphate composition reveals a compressive strength of at least 1 MPa.

Example 12

Determining Osteoinductive Potential of Bone Implant Materials

Assessment of ectopic bone formation after implantation in intramuscular or subcutaneous pockets within an athymic rat is the current standard for characterizing osteoinductive materials. This Example describes the use of the athymic rat model to assess bone implant materials prepared as described herein and to compare those compositions to other DBM formulations.

Six to seven week old male athymic rats (*Rattus norvegicus*, Crl:NIH-rnu nudes, Charles River Laboratories) are randomly implanted with four different test articles, two in the thoracic musculature (pectoris major muscle) and two in the hind limbs (quadriceps). Each animal receives an intraperitoneal (IP) injection of ketamine (100 mg/kg) and xylazine (10 mg/kg). Upon complete anesthetization, a small incision is made with a scalpel at the first implantation site, and the skin, subcutaneous tissue, and fascia are bisected with scissors. An intramuscular pouch is formed using pointed scissors to enter the desired muscle. The first cut is made in the same direction as the muscle fibers, and the scissors are spread to create a small pocket, which is held open while 0.1 ml of the test article is administered with forceps. The surgery is then repeated at the remaining three implant sites. If necessary, an additional half dose of ketamine/xylazine is administered to maintain anesthetization sufficient to complete the implantation procedure.

Daily clinical observations are performed on each animal for seven days post-implantation. Biweekly clinical observations are performed thereafter.

The test articles are retrieved six weeks following implantation. Animals are euthanized by $CO_2$ overdose immediately prior to retrieval. Tissue collections are limited to the implant material and approximately 0.5 cm margins of skeletal muscle and/or connective tissue. Tissue specimens are fixed in 10% neutral buffered formalin for a minimum of 12 hours and transferred in histological grade alcohol. Tissue specimens are bisected transversely at the implant midsection, routinely processed for paraffin embedding, cut onto glass slides, stained with hematoxylin and eosin, and coverslipped. If necessary, tissue specimens are additionally decalcified prior to histologic analysis.

Randomized histological slides, each representing a different intramuscular implant section, are presented to a pathologist in a blind fashion with respect to the implant administered. The amount of bone formation is scored using a 0-4 scale, with 0 indicating no evidence of bone formation, and 1, 2, 3, and 4 indicating <25%, 26-50%, 51-75%, and >75% of implant surface involved in new bone formation, respectively. New bone lined with osteoblasts and/or containing osteocytes within lacunae and cartilaginous cells with their matrix and bone marrow surrounded with trabeculae of new bone are all regarded as part of the bone neoformation process. The shape and size of the implant (relative to the original 5 mm cylinder), the distribution of new bone in the implant, and the nature of the implant matrix are also noted. Once the evaluation of the slides is completed, the key to group assignment is provided to the evaluator to summarize the results.

Example 13

Evaluation of Remodeling of Bone Implant Material

Implantation in a critically sized bone defect is a standard method of characterizing healing potential of bone grafting materials. This example describes implantation of the calcium phosphate composition of the invention as a bone graft material in critically-sized defects in a rabbit model.

Bilateral cylindrical defects are made in the distal femoral condyle of 4 to 5 Kg New Zealand White female rabbits in the following manner. The animal is anaesthetized using ketamine 30 mg/kg, xylazine 5 mg/kg, atropine 1-3 mg/kg intramuscularly and maintained on isoflurane after intubation. The skin at both knees and above areas is shaved and cleaned with 7.5% povidone-iodine and 70% isopropyl alcohol and the operating field draped properly. Through a lateral incision, the lateral femoral condyle is exposed. One 5.0 mm diameter and 10 mm deep bone defect will be created at each lateral femoral condyle by drilling under constant saline irrigation. The calcium phosphate composition of the invention is then packed into the defect as a bone graft material. Routine closure and suturing will follow. Typically some defects are left empty as a negative control and others are filled with morselized autologous bone graft harvested from the rabbit's iliac crest as a positive control.

Animals are monitored postoperatively for signs of infection, which is uncommon. All animals showing pain or discomfort will receive buprenorphine (0.02-0.05 mg/kg body weight) subcutaneously PRN every 12 hrs. They are observed and treated in a normal fashion in the recovery period. No restraining will be used. If any animal incurs a fracture, that rabbit is euthanized immediately.

The animals are sacrificed at appropriate time points after surgery using intravenous overdose of pentobarbital (Concentration: 390 mg/ml, 1 ml/10 lb body weight). This is consistent with the recommendations of the Panel on Euthanasia by the American Veterinary Medical Association. The outcome of the surgical graft implantation for all groups is evaluated by radiography, histology and histomorphometry.

AP radiographs are obtained post-op and at regular intervals. Animals will be anesthetized, placed in a prone position, and a single lateral radiograph will be taken. Care will be taken during all handling procedures to minimize loading to the defect site.

For histological evaluation, tissues will be fixed in 10% neutral buffered formalin. The specimens are processed for routine undecalcified sectioning. The tissues are processed and embedded in methylmethacrylate (MMA) and cut in the sagittal anatomical plane. Sections are stained with either Stevenel's blue stain or Goldner's trichrome stain for histological analysis. Histological sections are evaluated for areas of new bone formation, unhealed void or fibrous tissue, and residual implant material.

Example 14

Evaluation of Healing Potential of a Moldable Self Setting Macroporous Calcium Phosphate Cement The powder described in Example 8 was prepared as described in Example 9 and implanted as described in Example 13 and evaluated as compared to morselized autologous bone harvested from the iliac crest and empty untreated defects. Animals were sacrificed and tissues harvested after 12 weeks. Histological specimens showed near complete healing of both the test samples and the autologous bone. Healing was not observed in the untreated defects.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A self-setting, porous calcium phosphate composition comprising a calcium phosphate, an effervescent agent comprising carbonate and bicarbonate that reacts upon hydration of said composition to produce carbon dioxide as a gaseous component, and a biocompatible cohesiveness agent, wherein release of said gaseous component from said composition produces at least 5% porosity in a hardened material formed after said hydration of said composition, and wherein, after hardening, said hardened material has a compressive strength of 1 MPa or greater.

2. The composition of claim 1, wherein said calcium phosphate is selected from amorphous calcium phosphate, poorly crystalline calcium phosphate, hydroxyapatite, carbonated apatite (calcium-deficient hydroxyapatite), monocalcium phosphate, calcium metaphosphate, heptacalcium phosphate, dicalcium phosphate dihydrate, tetracalcium phosphate, octacalcium phosphate, calcium pyrophosphate, and tricalcium phosphate, or mixtures thereof.

3. The composition of claim 1, wherein said calcium phosphate is prepared using an amorphous calcium phosphate and a second calcium phosphate source.

4. The composition of claim 3, wherein said second calcium phosphate source is selected from poorly crystalline calcium phosphate, hydroxyapatite, carbonated apatite (calcium-deficient hydroxyapatite), monocalcium phosphate, calcium metaphosphate, heptacalcium phosphate, dicalcium phosphate dihydrate, tetracalcium phosphate, octacalcium phosphate, calcium pyrophosphate, and tricalcium phosphate.

5. The composition of claim 1, wherein said calcium phosphate has an average crystalline domain size of less than 100 nm.

6. The composition of claim 1, wherein pores of said composition have a pore size of between 1 and 1000 μm in diameter.

7. The composition of claim 1, wherein release of said gaseous component produces a porosity in the range of 5% to 60%.

8. The composition of claim 1, wherein said carbonate and bicarbonate are present in said composition at a molar ratio of 1:1 to 1:9.

9. The composition of claim 1, wherein said carbonate and bicarbonate are present in said composition at a 1:1 molar ratio.

10. The composition of claim 1, wherein said carbonate and bicarbonate are present in said composition at a 1:9 molar ratio.

11. The composition of claim 1, wherein said effervescent agent produces a continuous matrix of interconnected porosity throughout said composition.

12. The composition of claim 1, wherein said effervescent agent is present in an amount in the range of about 1 to about 40 wt%.

13. The composition of claim 1, wherein said biocompatible cohesiveness agent is selected from alginic acid, arabic gum, guar gum, xantham gum, gelatin, chitin, chitosan, chitosan acetate, chitosan lactate, chondroitin sulfate, N,0-carboxymethyl chitosan, a dextran, fibrin glue, glycerol, hyaluronic acid, sodium hyaluronate, a cellulose, a glucosamine, a proteoglycan, a starch, lactic acid, a pluronic, sodium glycerophosphate, collagen, glycogen, a keratin, silk, and mixtures thereof.

14. The composition of claim 13, wherein said cellulose is methylcellulose, carboxy methylcellulose, hydroxypropyl methylcellulose, or hydroxyethyl cellulose.

15. The composition of claim 1, wherein said biocompatible cohesiveness agent is present in an amount of less than about 1 to about 20 wt%.

16. The composition of claim 1, wherein said composition further comprises a biologically active agent.

17. The composition of claim 16, wherein said biologically active agent is selected from an antibody, a polypeptide, a protein, and a growth factor.

18. The composition of claim 17, wherein said protein is an osteogenic protein.

19. The composition of claim 18, wherein said osteogenic protein is selected from BMP-2, BMP-3, BMP-3b, BMP-4, BMP-5, BMP-6, BMP-7, BMP-8, BMP-9, BMP-10, BMP-11, BMP-12, BMP-13, BMP-14, BMP-15, BMP-16, BMP-17, and BMP-18.

20. The composition of claim 1, wherein said calcium phosphate has a calcium/phosphate (Ca/P) molar ratio of 1 to 1.67.

21. The composition of claim 1, wherein said composition comprises a compressive strength of between 1 MPa and 150 MPa.

22. The composition of claim 1, wherein said composition hardens in less than 30 minutes at 37° C.

23. A method of bone repair comprising administering to a subject in need thereof the self-setting, porous calcium phosphate composition of claim 1.

24. The composition of claim 1, wherein said composition comprises a physiologically-acceptable fluid.

25. The composition of claim 24, wherein said physiologically-acceptable fluid is selected from water, saline and a phosphate buffer.

26. The composition of claim 24, wherein said physiologically-acceptable fluid is a biological fluid.

27. The composition of claim 26, wherein said biological fluid is selected from blood, milk, urine, saliva, seminal or vaginal fluid, synovial fluid, lymph fluid, amniotic fluid, the fluid within the yolk sac, the chorion, the allantois of an egg, sweat, and tears.

28. The composition of claim 26, wherein said biological fluid comprises cells or cellular products.

29. The composition of claim 26, wherein said biological fluid comprises blood products derived from blood, blood components, bone marrow, red cells, or platelets.

* * * * *